US011814648B2

(12) United States Patent
Fossati et al.

(10) Patent No.: US 11,814,648 B2
(45) Date of Patent: Nov. 14, 2023

(54) FUNCTIONAL OLIGODENDROCYTES DERIVED FROM PLURIPOTENT STEM CELLS AND METHODS OF MAKING AND USING THE SAME

(71) Applicant: New York Stem Cell Foundation, Inc., New York, NY (US)

(72) Inventors: Valentina Fossati, New York, NY (US); Panagiotis Douvaras, New York, NY (US)

(73) Assignee: New York Stem Cell Foundation, Inc., New York, NY (US)

( * ) Notice: Subject to any disclaimer, the term of this patent is extended or adjusted under 35 U.S.C. 154(b) by 681 days.

(21) Appl. No.: 16/892,181

(22) Filed: Jun. 3, 2020

(65) Prior Publication Data

US 2020/0399595 A1 Dec. 24, 2020

Related U.S. Application Data

(63) Continuation of application No. 16/404,502, filed on May 6, 2019, now Pat. No. 10,676,716, which is a continuation of application No. 15/313,079, filed as application No. PCT/US2015/032274 on May 22, 2015, now Pat. No. 10,301,592.

(60) Provisional application No. 62/002,048, filed on May 22, 2014.

(51) Int. Cl.
*C12N 5/079* (2010.01)
*A61K 35/30* (2015.01)

(52) U.S. Cl.
CPC ............ *C12N 5/0622* (2013.01); *A61K 35/30* (2013.01); *C12N 2501/105* (2013.01); *C12N 2501/12* (2013.01); *C12N 2501/135* (2013.01); *C12N 2501/385* (2013.01); *C12N 2501/41* (2013.01); *C12N 2501/727* (2013.01); *C12N 2501/999* (2013.01); *C12N 2506/02* (2013.01); *C12N 2506/45* (2013.01); *C12N 2533/90* (2013.01)

(58) Field of Classification Search
CPC .............................. C12N 5/0622; A61K 35/30
USPC ......................................................... 435/355
See application file for complete search history.

(56) References Cited

U.S. PATENT DOCUMENTS

| 2010/0003751 A1 | 1/2010 | Revel et al. |
| 2010/0159595 A1 | 6/2010 | Zhang et al. |

FOREIGN PATENT DOCUMENTS

| WO | 2015/124725 A1 | 8/2015 |

OTHER PUBLICATIONS

Chambers (2009, Nature Biotechnology, 27:275-280).*
Bohnke (2022, Cellular Reprogramming, 14:5, pp. 304-313).*
Zou (2021, Frontiers in Molecular Biosciences, 8:593310, 11 pages).*
Alsanie et al., "Human Embryonic Stem Cell-Derived Oligodendrocytes: Protocols and Perspectives", Stem Cells and Development, vol. 22, No. 18, Jun. 12, 2013, pp. 2459-2476.
Baer et al., "Myelin-Mediated Inhibition of Oligodendrocyte Precursor Differentiation can be Overcome by Pharmacological Modulation of Fyn—RHoA and Protein Kinase C Signalling," Brain, vol. 132, No. 2, Feb. 2009, pp. 465-481.
Bai et al., "Hepatocyte Growth Factor Mediates MSCs Stimulated Functional Recovery in Animal Models of MS," Nature Neuroscience, vol. 15, No. 6, May 2012, pp. 862-870.
Chinese Search Report received for CN Application No. 201580033959. 8, dated Jan. 30, 2019, Translation.
Douvaras et al., "Efficient generation of myelinating oligodendrocytes from primary progressive multiple sclerosis patients by induced pluripotent stem cells", Stem Cell Reports, vol. 3, No. 2, Aug. 2014, pp. 250-259.
European Search Report and Search Opinion Received for EP Application No. 15796034.5, dated Oct. 17, 2017, 10 pages.
Hu et al., "Differentiation of human oligodendrocytes from pluripotent stem cells", Nature Protocols, vol. 4, No. 11, Oct. 2009, pp. 1614-1622.
Hu et al., "Differentiation of spinal motor neurons from pluripotent human stem cells", Nature Protocols, vol. 4, No. 9, Aug. 2009, pp. 1295-1304.
Hu et al., "Human oligodendrocytes from embryonic stem cells: conserved SHH signaling networks and divergent FGF effects", Development, vol. 136, May 2009, pp. 1443-1452.
International Preliminary Report on Patentability received for PCT Patent Application No. PCT/US2015/032274, dated Dec. 1, 2016, 12 pages.
International Search Report and Written Opinion received for PCT Patent Application No. PCT/US2015/032274, dated Sep. 15, 2015, 13 pages.
Mak et al., "Small Molecules Greatly Improve Conversion of Human-Induced Pluripotent Stem Cells to the Neuronal Lineage", Stem Cells International, vol. 2012, Jan. 2012, pp. 1-12.

(Continued)

*Primary Examiner* — Valarie E Bertoglio
(74) *Attorney, Agent, or Firm* — Goodwin Procter LLP

(57) ABSTRACT

Described is the efficient and robust generation of oligodendrocyte progenitor cells (OPCs) and oligodendrocytes from pluripotent stem cells (PSCs). The protocols provided recapitulate the major steps of oligodendrocyte differentiation, from neural stem cells to OLIG2$^+$ progenitors, and then to O4$^+$ OPCs, in a significantly shorter time than the 120-150 days required by previous protocols. Furthermore, O4$^+$ OPCs are able to differentiate into MBP$^+$ mature oligodendrocytes in vitro, and to myelinate axons in vivo when injected into immuno-compromised Shiverer mice, providing proof of concept that transplantation of PSC-derived cells for remyelination is technically feasible.

19 Claims, 16 Drawing Sheets

Specification includes a Sequence Listing.

(56) References Cited

OTHER PUBLICATIONS

Najm et al., "Rapid and Robust Generation of Functional Oligodendrocyte Progenitor Cells from Epiblast Stem Cells," Nature Methods, vol. 8, No. 11, Sep. 2011, pp. 957-962.
Office Action received for European Patent Application No. 15796034.5, dated Jul. 19, 2018, 7 pages.
Office Action received for European Patent Application No. 15796034.5, dated Oct. 28, 2019, 5 pages.
Qingwei et al., "Physiological Effects of Insulin", Medical Physiology 2nd Ed., Peking University Press, Jul. 31, 2007, 2 pages.
Sloane et al., "Hyaluronan Blocks Oligodendrocyte Progenitor Maturation and Remyelination through TLR2," PNAS, vol. 107, No. 25, Jun. 2010, pp. 11555-11560.
Stacpoole et al., "High Yields of Oligodendrocyte Lineage Cells from Human Embryonic Stem Cells at Physiological Oxygen Tensions for Evaluation of Translational Biology," Stem Cell Reports, vol. 1, No. 5, Oct. 2013, pp. 437-450.
Sundberg et al., "Production and isolation of NG2(+) oligodendrocyte precursors from human embryonic stem cells in defined serum-free medium", Stem Cell Research, vol. 5, No. 2, Sep. 2010, pp. 91-103.
Translation of Chinese Office Action received for CN Application No. 201580033959.8, dated Jan. 30, 2019.
Antel, J. et al., "Primary progressive multiple sclerosis: part of the MS disease spectrum or separate disease entity?", Acta. Neuropathol., (2012), vol. 123, pp. 627-638.
Bartzokis, G., "Brain Myelination in Prevalent Neuropsychiatric Developmental Disorders: Primary and Comorbid Addiction," Adolesc Psychiatry, (2005) 29: pp. 55-96.
Behrendt, G. et al., "Dynamic changes in myelin aberrations and oligodendrocyte generation in chronic amyloidosis in mice and men," Glia, (2013), 61: pp. 273-286.
Bernstein, H. et al., "Glial cells as key players in schizophrenia pathology: recent insights and concepts of therapy," Schizophr. Res., (2015), 161: pp. 4-18.
Boulting, G. L. et al., "A functionally characterized test set of human induced pluripotent stem cells," Nat Biotechnol. (Mar. 2011), 29(3): pp. 279-286.
Douvaras, P. et al., "Generation and isolation of oligodendrocyte progenitor cells from human pluripotent stem cells," Nat Protoc (2015), 10, pp. 1143-1154.
Fennema-Notestine, C. et al., "In vivo evidence of cerebellar atrophy and cerebral white matter loss in Huntington disease," Neurology, (Sep. 2004), 63(6), pp. 989-995.
Gil, J. et al., "Vitronectin promotes oligodendrocyte differentiation during neurogenesis of human embryonic stem cells," FEBS Letters, vol. 583, Issue 3, (2009), pp. 561-567.
Goldman, S. A., et al., "Glial Progenitor Cell-Based Treatment and Modeling of Neurological Disease," Science, (Oct. 26, 2012), 338(6106), pp. 491-495.
Han, S. S. W. et al., "Constructing and Deconstructing Stem Cell Models of Neurological Disease," Neuron, (2011), vol. 70, issue 4, pp. 626-644.
Hauser, S. L. et al., "Multiple sclerosis: Prospects and promise," Ann. Neurol., (2013), 74, pp. 317-327.
Hu, Z. et al., "Hepatocyte growth factor enhances the generation of high-purity oligodendrocytes from human embryonic stem cells," Differentiation, (2009), 78, pp. 177-184.
Irion, S. et al., "Directed Differentiation of Pluripotent Stem Cells: From Developmental Biology to Therapeutic Applications," Cold Spring Harb. Sym, (2008), 73, pp. 101-110.
Izrael, M. et al., "Human oligodendrocytes derived from embryonic stem cells: Effect of noggin on phenotypic differentiation in vitro and on myelination in vivo," Mol Cell Neurosci., (2007) 34(3), pp. 310-323.
Jakovcevski, I. et al., "Oligodendrocyte development and the onset of myelination in the human fetal brain," Front Neuroanat., (2009), 3:5, pp. 1-15.
James, D. et al., "TGFR/activin/nodal signaling is necessary for the maintenance of pluripotency in human embryonic stem cells," Development, vol. 132(6), (2005), pp. 1273-1282.
Kang, J. et al., "Granulocyte Colony-Stimulating Factor Minimizes Negative Remodeling of Decellularized Small Diameter Vascular Graft Conduits but Not Medial Degeneration," Ann. Vase. Sur. (2013), 27(4), pp. 487-496.
Kassmann, C. M. et al., "Axonal loss and neuroinflammation caused by peroxisome-deficient oligodendrocytes," Nature Genet., (2007), 39, pp. 969-976.
Lee, S. et al., "A rapid and reproducible assay for modeling myelination by oligodendrocytes using engineered nanofibers," Nat Protoc. (2013), 8(4), pp. 771-782.
Liu, Y et al., "OLIG gene targeting in human pluripotent stem cells for motor neuron and oligodendrocyte differentiation," Nat Protoc., (2011), 6, pp. 640-655.
Miller, R. H. et al., "Patterning of spinal cord oligodendrocyte development by dorsally derived BMP4," J. Neurosci. Res., (2004), 76, pp. 9-19.
Murry, C. E., et al., "Differentiation of Embryonic Stem Cells to Clinically Relevant Populations: Lessons from Embryonic Development," Cell, (2008), 132, pp. 661-680.
Nistor, G. I. et al., "Human Embryonic Stem Cells Differentiation into Oligodendrocytes in High Purity and Myelinate After Spinal Cord Transplantation," Glia, (2005), 49, pp. 385-396.
Novitch, B. G. et al., "A Requirement for Retinoic Acid-Mediated Transcriptional Activation in Ventral Neural Patterning and Motor Neuron Specification," Neuron, (2003), 40, pp. 81-95.
Numasawa-Kuroiwa, Y. et al., "Involvement of ER Stress in Dysmyelination of Pelizaeus-Merzbacher Disease with PLP1 Missense Mutations Shown by iPSC-Derived Oligodendrocytes," Stem Cell Rep., (2014), 2, pp. 648-661.
Patani, R. et al., "Retinoid-independent motor neurogenesis from human embryonic stem cells reveals a medial columnarground state," Nature Communications, (2011), 2:214, pp. 1-10.
Pouya, A. et al., "Human Induced Pluripotent Stem Cells Differentiation into Oligodendrocyte Progenitors and Transplantation in a Rat Model of Optic Chiasm Demyelination," PLoS One, (2011), 6:e27925, pp. 1-10.
Rice, C. M. et al., "Primary progressive multiple sclerosis: progress and challenges," J Neurol. Neurosurg. Ps., (2013), 84, pp. 1100-1106.
Sim, F. J. et al., "CD140a identifies a population of highly myelinogenic, migration-competent, and efficiently engrafting human oligodendrocyte progenitor cells," Nat. Biotechnol., (2011), 29, pp. 934-941.
Sim, F. J. et al., "Expression of the POU-Domain Transcription Factors SCIP/Oct.-6 and Brn-2 is Associated with Schwann Cell but Not Oligodendrocyte Remyelination of the CNS," Molec. Cell. Neurosci., (2002), 20, pp. 669-682.
Song, B. et al., "Neural differentiation of patient specific iPS cells as a novel approach to study the pathophysiology of multiple sclerosis," Stem Cell Res., (2012), 8, pp. 259-273.
Supplementary European Search Report dated Oct. 17, 2017, regarding EP 15796034.
Tomassy, G. S. et al., "How big is the myelinating orchestra? Cellular diversity within the oligodendrocyte lineage: facts and hypotheses," Front. Cell. Neurosci., (2014), 8:201, pp. 1-11.
Wang, S. et al., "Human IPSC-Derived Oligodendrocyte Progenitor Cells can Myelinate and Rescue a Mouse Model of Congenital Hypomyelination," Cell Stem Cell, (2013), 12, pp. 252-264.
Warren, L. et al., "Highly Efficient Reprogramming to Pluripotency and Directed Differentiation of Human Cells with Synthetic Modified mRNA," Cell Stem Cell, (2010), 7, pp. 618-630.
Wichterle, H. et al., "Directed Differentiation of Embryonic Stem Cells into Motor Neurons," Cell, (2002), 110, pp. 385-397.
Windrem, M. S. et al., "Neonatal Chimerization with Human Glial Progenitor Cells Can Both Remyelinate and Rescue the Otherwise Lethally Hypomyelinated Shiverer Mouse," Cell Stem Cell, (2008), 2, pp. 553-565.
Yamada, M. et al., "Human oocytes reprogram adult somatic nuclei of a type 1 diabetic to diploid pluripotent stem cells," Nature, (2014), 510, pp. 533-536.

* cited by examiner

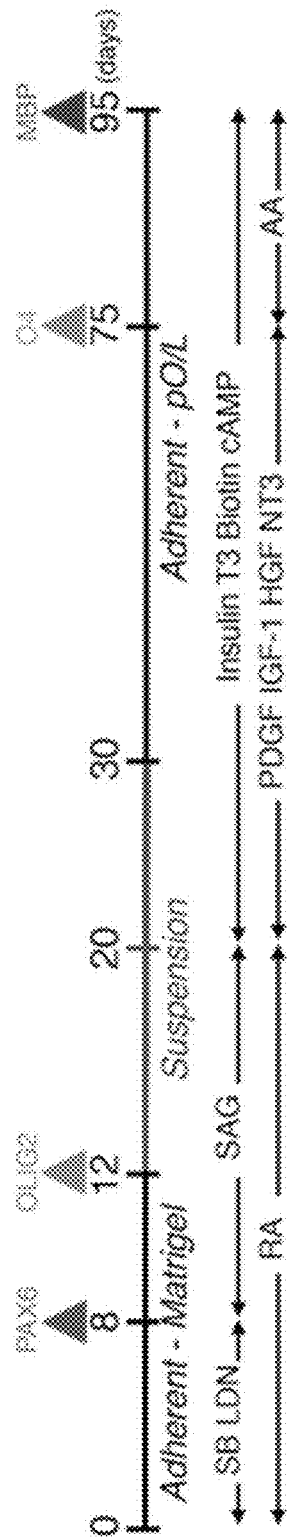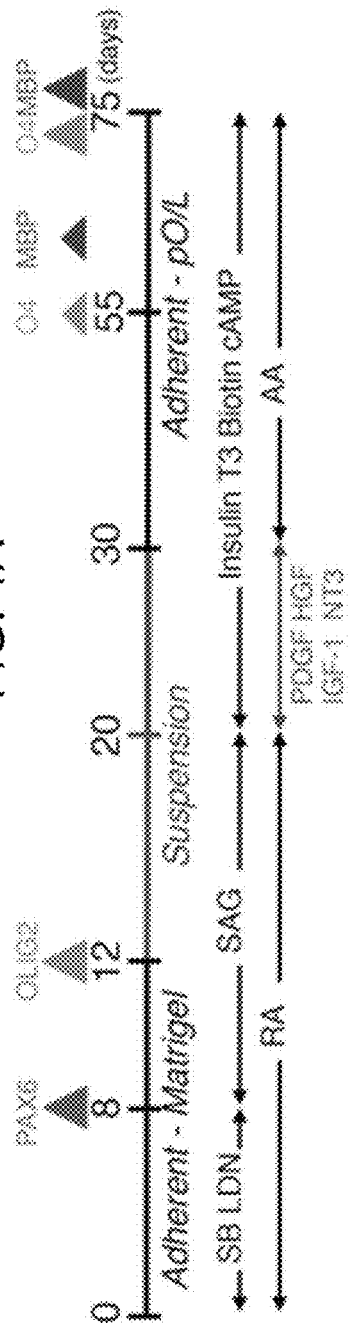

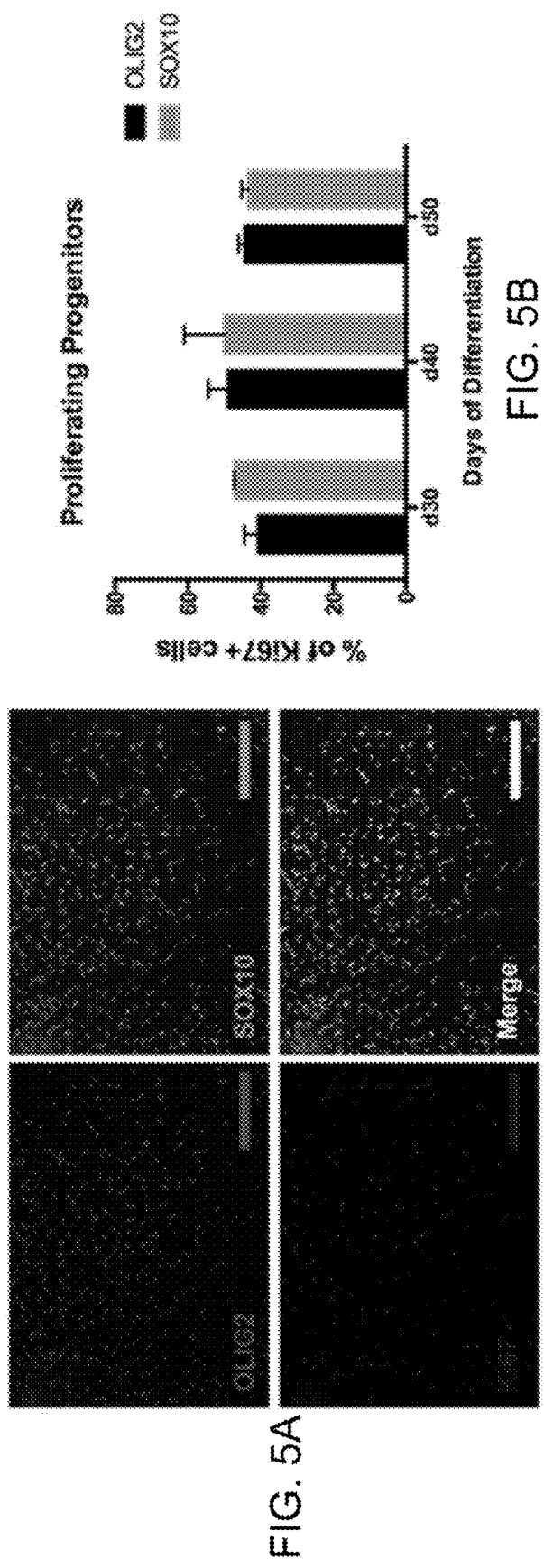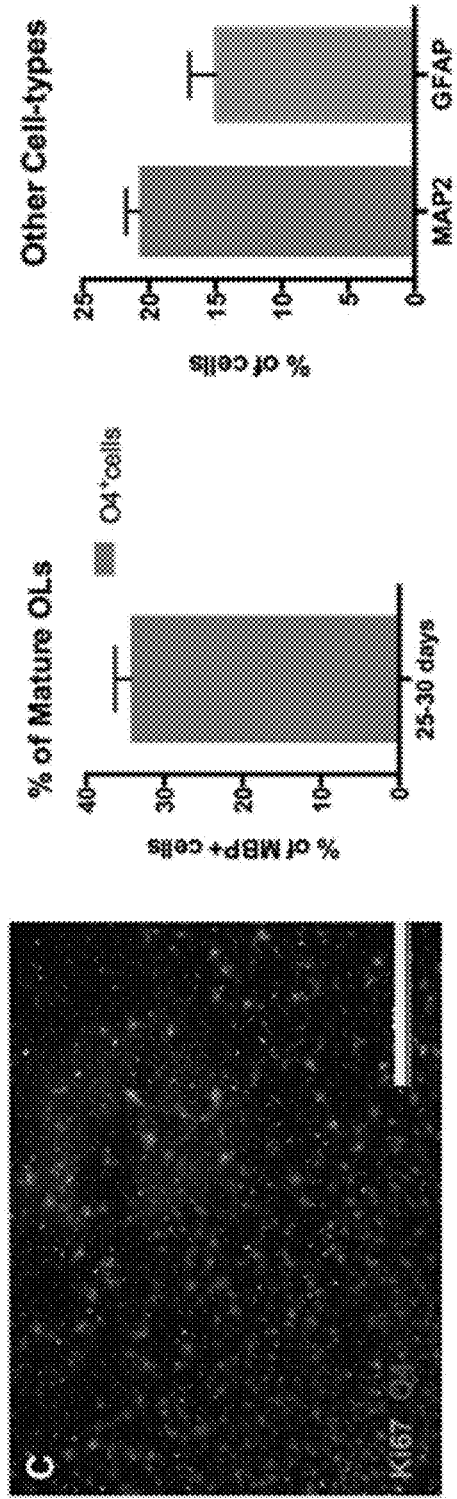

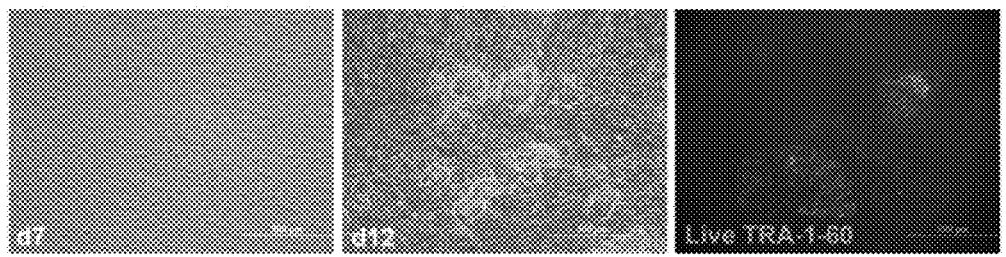
FIG. 8A
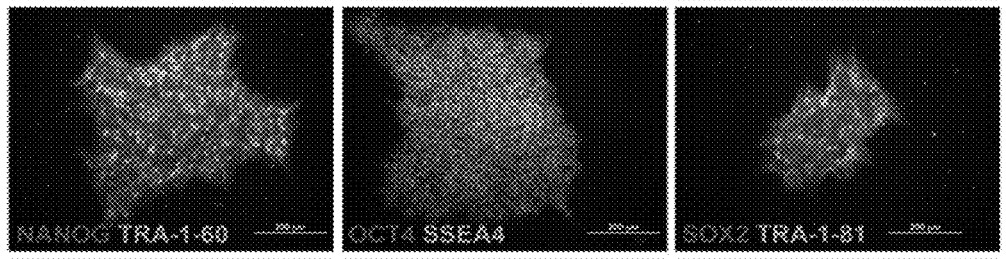
FIG. 8B
FIG. 8C
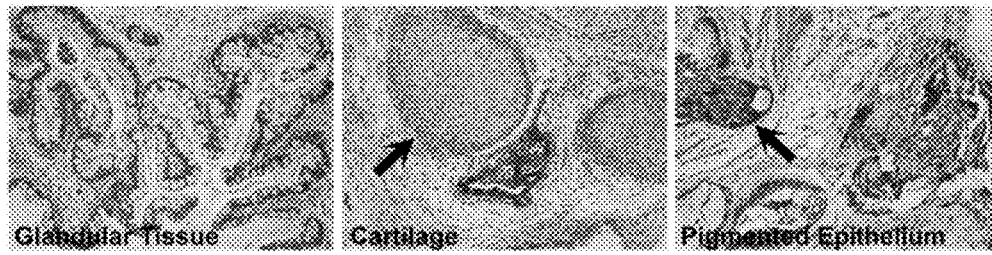
FIG. 8D
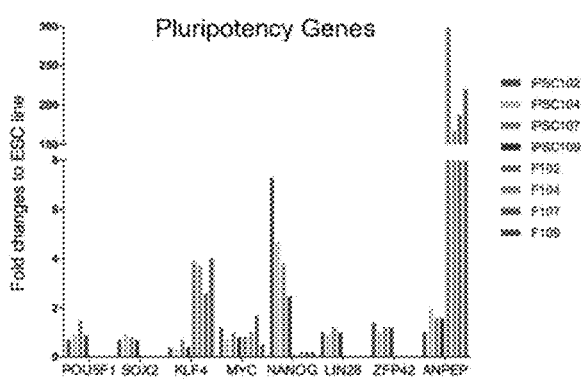
FIG. 8E
FIG. 8F

| iPS line | MS Type | Sex | Age |
|---|---|---|---|
| 106 | Relapsing-Remitting | Male | 24 |
| 112 | Relapsing-Remitting | Female | 63 |
| 108 | Relapsing-Remitting | Female | 50 |
| 105 | Secondary Progressive | Female | 63 |
| 103 | Secondary Progressive | Male | 42 |
| 101 | Secondary Progressive | Male | 58 |
| 105 | Secondary Progressive | Female | 63 |
| 102 | Primary Progressive | Male | 56 |
| 107* | Primary Progressive | Male | 61 |
| 109 | Primary Progressive | Female | 50 |
| 104 | Primary Progressive | Female | 62 |
| 111 | Healthy Control | Male | 28 |
| 110* | Healthy Control | Male | 66 |
| 130 | Healthy Control | Male | 52 |
| 197 | Healthy Control | Male | 66 |
| 223 | Healthy Control | Female | 50 |

*=brothers

FIG. 13

FUNCTIONAL OLIGODENDROCYTES DERIVED FROM PLURIPOTENT STEM CELLS AND METHODS OF MAKING AND USING THE SAME

CROSS-REFERENCE TO RELATED APPLICATIONS

This application is a continuation application of U.S. application Ser. No. 16/404,502 filed May 6, 2019, now issued as U.S. Pat. No. 10,676,716; which is a continuation application of U.S. application Ser. No. 15/313,079 filed Nov. 21, 2016, now issued as U.S. Pat. No. 10,301,592; which is a 35 USC § 371 National Stage application of International Application No. PCT/US2015/032274 filed May 22, 2015, now expired; which claims the benefit under 35 USC § 119(e) to U.S. Application Ser. No. 62/002,048 filed May 22, 2014, now expired. The disclosure of each of the prior applications is considered part of and is incorporated by reference in the disclosure of this application.

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

INCORPORATION OF SEQUENCE LISTING

The material in the accompanying sequence listing is hereby incorporated by reference into this application. The accompanying sequence listing text file, named NYSC1250-3_ST25.txt, was created on May 28, 2020 and is 3 KB in size. The file can be accessed using Microsoft Word on a computer that uses Windows OS.

BACKGROUND OF THE INVENTION

Oligodendrocytes are central nervous system cells present in vertebrates. They produce a laminated, lipid-rich myelin sheath that wraps the neuronal axons and creates defined segments of electrical insulation to maximize the speed of action potential conduction. Myelin is also important for axonal integrity and survival, and it has been shown that even small changes affecting oligodendrocyte metabolism can lead to neurodegeneration. Kassmann, C. M. et al., *Nature Genet.* 39:969-976 (2007). The myelination process is particularly important in humans, as human brains have a higher content of myelinated neurons (white matter) and myelination continues after birth and throughout life. Bartzokis, G., *Adolescent Psychiat.* 29:55-96 (2005). This suggests that oligodendrocytes are not merely providing inert insulation, but rather that myelination is a dynamic process, affecting cognitive function and even behavior.

Multiple sclerosis (MS), adrenoleukodystrophy, vanishing white matter disease, Pelizaeus-Merzbacher disease, and leukodystrophies are examples of demyelinating or dysmyelinating disorders. In addition, a critical role for oligodendrocytes is emerging in many other neurological disorders and neurodegenerative conditions, including amyotrophic lateral sclerosis, Huntington's disease, Alzheimer's disease, and schizophrenia. Bernstein, H. G. et al., *Schizophr. Res.* 161:4-18 (2015); Behrendt, G. et al., *Glia* 61:273-286 (2013); Kang, J. et al., *Ann. Vasc. Surg.* 27:487-496 (2013); Fennema-Notestine, C. et al., *Neurology* 63:989-995 (2004). Human oligodendrocyte progenitor cells (OPCs) can be used to develop in vitro myelination assays, to screen for myelinating compounds, and ultimately could become a source for autologous cell replacement therapies. In particular, the generation of patient-specific cells from induced pluripotent stem cells (iPSCs) for autologous cell therapy has recently emerged as a promising concept. Wang, S. et al., *Cell Stem Cell* 12:252-264 (2013); Goldman, S. A. et al., *Science* 338:491-495 (2012).

Studies of human oligodendrocyte biology and human myelination have been hampered by the limited access to primary cells from biopsies or autopsies. Pluripotent stem cells (PSCs) have been used within the last two decades as an alternative, useful source from which any desired cell type can be generated. This has been achieved by recapitulating in vitro the fundamental steps of embryonic development. Irion, S. et al., *Cold Spring Harb. Sym.* 73:101-110 (2008). Notably, most of the critical pathways of lineage commitment are highly conserved between mice and humans and therefore, insights gained from mouse developmental biology have been successfully applied to produce numerous cell types, including oligodendrocytes, from human PSCs (hPSCs). Murry, C. E. et al., *Cell* 132:661-680 (2008).

In mice, oligodendrocyte precursors arise within the motor neuron progenitor (pMN) domain. During mouse embryonic development, retinoic acid (RA) and sonic hedgehog (SHH) pathways are critical in defining the pMN domain. This finding has been exploited in in vitro cultures to convert neuroepithelial cells into progenitors of the pMN domain, expressing the transcription factor OLIG2. Wichterle, H. et al., *Cell* 110:385-397 (2002). RA at a concentration of 10 µM has been used in most methods to differentiate human embryonic stem cells (hESCs) to oligodendrocytes. Izrael, M. et al., *Mol. Cell. Neurosci.* 34:310-323 (2007); Nistor, G. I. et al., *Glia* 49:385-396 (2005). The Zhang laboratory demonstrated that SHH is necessary for the induction of OLIG2$^+$ NKX2.2$^+$ progenitors, and for their transition to oligodendrocyte progenitor cells (OPCs) expressing SOX10, PDGFRα and ultimately O4. Hu, B. Y. et al., *Development* 136:1443-1452 (2009a). The appearance of OPCs in vitro is significantly delayed in the human model compared to the mouse model; there is a protracted period of 10 weeks between the peak of OLIG2$^+$ progenitors and the peak of OPCs in the human model. Hu, B. Y. et al., *Nat. Protoc.* 4:1614-1622 (2009b).

Several groups have devised protocols to differentiate PSCs to OPCs. Numasawa-Kuroiwa, Y. et al.; *Stem Cell Rep.* 2:648-661 (2014); Stacpoole, S. R. et al., *Stem Cell Rep.* 1:437-450 (2013); Wang et al., (2013); Liu, Y. et al., *Nat. Protoc.* 6:640-655 (2011); Sim, F. J. et al., *Nat. Biotechnol.* 29:934-941 (2011). However, these differentiation protocols are lengthy and inefficient; their practical application is limited by required culture times of over 120 days to obtain OPCs expressing the O4 antigen. Furthermore, the reported efficiencies of O4$^+$ cells obtained range from 4% to 47%. In addition, many differentiation protocols have been optimized using only one or two hESC lines, and their reproducibility with iPSC lines is controversial. Alsanie, W. et al., *Stem Cells Devel.* 22:2459-2476 (2013).

Therefore, an improved oligodendrocyte differentiation protocol that generates large numbers of purified OPCs in a relatively short time is highly desirable. Moreover, this protocol should be reproducible among different PSC lines and should be highly efficient.

SUMMARY OF THE INVENTION

Some of the main aspects of the present invention are summarized below. Additional aspects are described in the Detailed Description of the Invention, Examples, Figures, and Claims sections of this disclosure. The description in each section of this disclosure is intended to be read in conjunction with the other sections. Furthermore, the various embodiments described in each section of this disclosure can be combined in various different ways, and all such combinations are intended to fall within the scope of the invention.

The present invention provides a robust differentiation protocol that generates 40% to 70% O4+ OPCs within 75 days. Douvaras, P. et al., *Stem Cell Rep.* 3:250-259 (2014) (incorporated herein by reference in its entirety). Also provided is a strategy for obtaining about 30% O4+ OPCs after just 55 days of differentiation, resulting in a substantial cost reduction. Douvaras, P. et al., *Nat. Protoc.* (2015) (incorporated herein by reference in its entirety). When purified, the O4+ cells are able to engraft and, in short term (16 weeks) transplantation studies into the shiverer (shi/shi) mouse model, show comparable myelination potential to human fetal OPCs. OPCs are purified by fluorescent activated cell sorting (FACS) at the stage where they express O4 rather than PDGFRα, which eliminates contaminant cells and minimizes the tumorigenic potential. Our protocol was validated using more than nine hPSC lines, with very consistent results seen for each line. Therefore, the present invention provides a highly reproducible protocol to efficiently derive OPCs and mature oligodendrocytes from PSCs, including embryonic stem cells (ESCs) and iPSCs.

In one aspect, the invention provides a method of generating OLIG2+ OPCs, the method comprising: (a) preparing PSC colonies by (i) seeding PSCs at low density on a surface; and (ii) culturing the PSCs in an adherent culture for 1-2 days, thereby preparing PSC colonies; (b) culturing the PSC colonies to confluence in a medium comprising a low concentration of RA, at least one inhibitor of transforming growth factor beta (TGFβ) signaling, and at least one inhibitor of bone morphogenetic protein (BMP) signaling, wherein the first day of said culturing is day 0; (c) culturing the confluent cells in a medium comprising Smoothened Agonist (SAG; 3-chloro-N-[(1r,4r)-4-(methylamino)cyclohexyl]-N-[3-(pyridin-4-yl)benzyl]benzo[b]thiophene-2-carboxamide) and a low concentration of RA until cells are overconfluent, wherein the cells express OLIG2; thereby generating OLIG2+ OPCs.

In another aspect, the invention provides a method of generating O4+ OPCs, the method comprising: (a) culturing three-dimensional cell aggregates of OLIG2+ OPCs in suspension in a medium comprising an agonist of Smoothened and a low concentration of RA for about 8 days; (b) culturing the cell aggregates in suspension in a medium comprising platelet-derived growth factor (PDGF), hepatocyte growth factor (HGF), insulin-like growth factor 1 (IGF-1), and neurotrophin 3 (NT3) for about 10 days; (c) re-plating the cell aggregates at a density of 2 spheres/cm$^2$; and (d) culturing the cell aggregates in an adherent culture in a medium comprising (i) ascorbic acid (AA) or (ii) PDGF, HGF, IGF-1, and NT3 until cells are O4+; thereby generating O4+ OPCs. Mature oligodendrocytes can be generated by culturing the O4+ OPCs in the absence of PDGF, HGF, IGF-1, and NT3 for about three weeks; thereby generating oligodendrocytes, wherein the oligodendrocytes express myelin basic protein (MBP+).

In a further aspect, the invention provides a method of generating oligodendrocytes, the method comprising: (a) preparing PSC colonies by (i) seeding PSCs at low density on a surface; and (ii) culturing the PSCs in an adherent culture for 1-2 days, thereby preparing PSC colonies; (b) culturing the PSC colonies to confluence in a medium comprising a low concentration of RA, at least one inhibitor of TGFβ signaling, and at least one inhibitor of BMP signaling, wherein the first day of said culturing is day 0; (c) culturing the confluent cells in a medium comprising an agonist of Smoothened and a low concentration of RA until cells are overconfluent, wherein the cells are OLIG2+ OPCs; (d) lifting the cells from the surface, thereby allowing formation of three-dimensional cell aggregates; (e) culturing the cell aggregates in suspension in a medium comprising an agonist of Smoothened and a low concentration of RA for about 8 days; (f) culturing the cell aggregates in suspension in a medium comprising PDGF, HGF, IGF-1, and NT3 for about 10 days; (g) re-plating the cell aggregates at a density of 2 spheres/cm$^2$; (h) culturing the cell aggregates in an adherent culture in a medium comprising (i) AA or (ii) PDGF, HGF, IGF-1, and NT3 until cells are O4+, thereby generating O4+ OPCs; and (i) culturing the O4+ OPCs in a medium comprising AA and lacking PDGF, HGF, IGF-1, and NT3 until cells are MBP+; thereby generating oligodendrocytes.

Another aspect of the invention is a method of generating oligodendrocytes, the method comprising: (a) culturing PSCs in an adherent culture as a monolayer in a medium comprising a low concentration of RA, (i) with dual SMAD inhibition from day 0 to day 8, and (ii) with SHH or an agonist of Smoothened from day 8 to day 12, to produce OLIG2+ cells; (b) enriching for OLIG2+ cells by culturing the cells of step (a) in suspension (i) from day 12 to day 20 in a medium comprising SHH or an agonist of Smoothened and a low concentration of RA, and (ii) from day 20 to day 30 in a medium comprising PDGF, HGF, IGF-1, and NT3; (c) culturing the cells of step (b) in an adherent culture in a medium comprising PDGF, HGF, IGF-1, and NT3 from day 30 to day 75 to produce O4+ OPCs; and (d) culturing the O4+ OPCs in adherent culture in a medium comprising AA and lacking PDGF, HGF, IGF-1, and NT3 from day 75 to day 95; thereby generating oligodendrocytes.

An additional aspect of the invention is a method of generating oligodendrocytes, the method comprising: (a) culturing PSCs in an adherent culture as a monolayer in a medium comprising a low concentration of RA, (i) with dual SMAD inhibition from day 0 to day 8, and (ii) with SHH or an agonist of Smoothened from day 8 to day 12, to produce OLIG2+ cells; (b) enriching for OLIG2+ cells by culturing the cells of step (a) in suspension (i) from day 12 to day 20 in a medium comprising SHH or an agonist of Smoothened and a low concentration of RA, and (ii) from day 20 to day 30 in a medium comprising PDGF, HGF, IGF-1, and NT3; and (c) culturing the cells of step (b) in an adherent culture in a medium comprising AA and lacking PDGF, HGF, IGF-1, and NT3 from day 30 to day 60; thereby generating oligodendrocytes.

Also provided is a method of identifying a compound that promotes myelination, the method comprising: (a) generating an oligodendrocyte by a method of the invention; (b) contacting the oligodendrocyte with a candidate compound; and (c) determining whether the candidate compound promotes neuron myelination.

Another embodiment is a method of treating a neurological disease or disorder in a subject, the method comprising: (a) generating oligodendrocytes by a method of the invention; and (b) administering to the subject an effective amount of the oligodendrocytes, wherein the oligodendrocytes promote myelinogenesis in the nervous system of the subject; thereby treating the neurological disease in the subject.

The invention also encompasses oligodendrocyte progenitor cells and oligodendrocytes produced by the methods of the invention, and non-human mammals comprising them.

BRIEF DESCRIPTION OF THE FIGURES

FIGS. 1A-1B show a timeline of oligodendrocyte differentiation following Option A (FIG. 1A) and Option B (FIG. 1B). Triangles represent the recommended time points to evaluate the expression of stage-specific markers through imunofluorescence. SB: SB431542; LDN: LDN193189; SAG: Smoothened Agonist; T3: triiodothryonine; RA: all trans retinoic acid; PDGF: platelet derived growth factor; HGF: hepatocyte growth factor; IGF-I: insulin like growth factor-1; NT3: neurotrophin 3; AA: ascorbic acid.

FIG. 2A shows live imaging and flow cytometric quantification of OLIG2-GFP cells at day 14 of differentiation under different conditions for RA and SHH. RA at a concentration of 100 nM from day 0 results in the highest yield of GFP$^+$ cells. FIG. 2B shows a comparison between the addition of SHH or SAG at day 8 to the best RA condition, via live imaging and FACS-analysis. Negative: hESC line RUES1. FIG. 2C shows temporal gene expression profile of PAX6, OLIG2 and NKX2.2 under optimal RA and SHH conditions. Error bars are SEM (N=3). Comparable results are obtained using RUES1 cells and the OLIG2-GFP reporter line. FIG. 2D shows an assessment of sphere-formation for unsorted cells, sorted GFP$^+$ cells, or GFP$^-$ cells. Only GFP$^+$ cells form spheres, providing enrichment to the GFP$^+$ population.

FIG. 3A shows mRNA levels for OLIG2, PTCH1 and SHH at day 14 of differentiation between cultures with RA from d0 and SHH/SAG from d8, compared to cells that were exposed only to RA from d0. Endogenous SHH levels are higher in the samples that were not exposed to SHH/SAG. Error bars are SEM (N=3). FIG. 3B shows FACS-analysis for O4$^+$ cells at day 75 of differentiation between cells that were exposed to RA only, or RA and SAG, in the first 12 days of differentiation. A 56% decrease in the O4$^+$ population was observed in the cells that were not provided with SAG in the initial steps of differentiation. Negative Control: APC-conjugated secondary antibody only.

FIG. 3C shows live imaging and FACS-analysis at day 14 of differentiation under different SMAD inhibitors. A substantial population of GFP$^+$ cells is present only under the dual inhibition of SMAD proteins, indicating a synergistic effect between RA and the dual inhibition of SMAD. DSi: Dual SMAD inhibition; SB: SB431542; LDN: LDN189193.

FIG. 4A shows a diagram of the differentiation protocol from hPSCs to mature oligodendrocytes. FIGS. 4B-4M are sequential steps of in vitro oligodendrocyte differentiation of RUES1 cells showing: PAX6$^+$ neural stem cells at day 8 (FIG. 4B), phase contrast of the multilayered structures at day 12 (FIG. 4C), OLIG2$^+$ NKX2.2$^+$ pre-OPC at day 18 (FIG. 4D), SOX10$^+$ OLIG2$^+$ early OPCs (FIG. 4E), live imaging of O4$^+$ late OPCs (FIG. 4F), cropped image of O4$^+$ cells to highlight the ramified processes (FIG. 4G), O4$^+$ OPCs co-expressing OLIG2 (FIG. 4H), O4$^+$ OPCs co-expressing SOX10 (FIG. 4I), sorted O4$^+$ OPCs co-expressing SOX10 and NG2 (FIG. 4J), terminally differentiated MBP$^+$ oligodendrocytes at low (FIG. 4K), and higher (×64) magnification (FIG. 4L), MAP2$^+$ and GFAP$^+$ cells in the oligodendrocyte cultures (FIG. 4M). PSC: pluripotent stem cell; NSC: neural stem cell; OPC: oligodendrocyte progenitor cell; OL: oligodendrocyte; pO/L: poly-L-ornithine/Laminin.

FIGS. 5A-5E show proliferative oligodendrocytes and other neural cell-types. FIG. 5A shows representative immunofluorescence staining at d50 of differentiation for OLIG2, SOX10 and Ki67. There is an almost complete co-localization between OLIG2 and SOX10. FIG. 5B shows temporal quantification of Ki67$^+$ cells showing the percentage of OLIG2$^+$ and SOX10$^+$ progenitors that proliferate between d30 and d50 of differentiation. Error bars are SEM (N=2). FIG. 5C shows an immunofluorescence image of a culture at d73 showing a high number of O4$^+$ cells, but hardly any cells co-express Ki67. FIG. 5D shows the percentage of O4$^+$ cells that co-express MBP 4 weeks after growth-factor removal (Glial Medium). Error bar is SEM (N=4). FIG. 5E shows the percentage of MAP2$^+$ neurons and GFAP$^+$ astrocytes to total number of cells in three independent experiments at d78-d88 of differentiation. Error bars are SEM (N=3).

FIGS. 6A-6C show representative fields at low magnification; the number of O4$^+$ cells increases with time. FIGS. 6D-6F show higher magnification images of FIGS. 6A-6C, respectively, to highlight the morphology of the cells. FIG. 6G shows representative examples of O4$^+$ cell frequencies calculated by flow cytometry at different time points using the Option B ("fast") protocol (day 55, day 63 and day 75) and the Option A ("original") protocol. Scale bars: 500 µm (6A-6C); 200 µm (FIGS. 6D-6F).

FIG. 7A shows PAX6$^+$ neural stem cells at day 8 of differentiation (PAX6, green; nuclei are stained with DAPI, blue). FIG. 7B shows typical morphology of the culture at day 12, depicting three-dimensional structures. FIG. 7C shows expression of OLIG2 and NKX2.2 at day 12 as shown through immunofluorescent analysis (OLIG2, green; NKX2.2, red; nuclei are stained with DAPI, blue). FIG. 7D shows spheres selection: arrows indicate the good spheres, which are round-shape, golden/brown in color, with darker core and with a diameter between 300 µm and 800 µm. The exclamation mark indicates a pair of joined spheres that can be broken into single spheres by gentle pipetting. Aggregates that should be avoided are small and transparent (arrowheads) or very large and irregular in shape, usually derived by mechanical digestion (star). FIG. 7E shows immunofluorescent staining of progenitor cells at day 56, co-expressing NKX2.2 (green), SOX10 (red) and OLIG2 (blue). FIG. 7F shows O4 (green) live staining showing the highly ramified morphology of the cells. FIG. 7G shows MBP$^+$ (red) oligodendrocytes at the end of the differentiation (nuclei are stained with DAPI, blue). FIG. 7H shows morphology of MBP$^+$ (red) oligodendrocytes at higher magnification (64×). MAP2$^+$ (green) and GFAP$^+$ (blue) cells are also present in the culture. FIG. 7I shows that purified O4$^+$ cells 24 hours after sorting still retain the typical ramified morphology. Scale bars: 500 µm (FIG. 7A, 7B, 7G); 200 µm (FIG. 7C, 7E, 7F, 7I); 1 mm (FIG. 7D).

FIG. 8A-8F shows the generation and characterization of PPMS iPSC lines. FIG. 8A shows mRNA/miRNA reprogramming of PPMS lines, showing representative skin fibroblasts at day 7, iPSC-like colonies evident at day 12, and TRA-1-60$^+$ colonies at day 15 of reprogramming. FIG. 8B shows immunofluorescence of PPMS-iPSC 102 for pluripotency markers. FIG. 8C shows immunofluorescence after in vitro spontaneous differentiation through embryoid bodies for endodermal marker AFP, mesodermal marker αSMA and ectodermal marker βIII-tubulin. Nuclei are stained with DAPI. FIG. 8D shows H&E stained sections of in vivo teratoma formation after injection of PPMS iPSCs into immunodeficient mice, showing representative structures from glandular tissue (endoderm), cartilage (mesoderm) and pigmented epithelium (ectoderm). FIG. 8E shows pluripotency gene expression of undifferentiated PPMS-iPSC and parental fibroblasts, relative to a hESC line. ANPEP gene is specific for fibroblasts. FIG. 8F shows cytogenetic analysis; all PPMS-iPSC lines show a normal karyotype.

FIGS. 10A-10I are sequential steps of in vitro oligodendrocyte differentiation of PPMS iPSC showing: PAX6$^+$ cells at day 8 (FIG. 10A), multilayered structures in phase contrast at day 12 (FIG. 10B), OLIG2$^+$ and NKX2.2$^+$ cells at day 12 (FIG. 10C), SOX10$^+$ OLIG2$^+$ early OPCs (FIG. 10D), live imaging of O4$^+$ late OPCs at day 73 (FIG. 10E), cropped image of O4$^+$ cells to highlight the ramified processes (FIG. 10F), terminally differentiated MBP$^+$ oligodendrocytes in low (FIG. 10G), and higher (×64) magnification (FIG. 10H), MAP2$^+$ cells in the oligodendrocyte cultures (FIG. 10D. FIG. 10J shows quantification of O4$^+$ cells after 75 days of differentiation from RUES1 and PPMS iPSCs via FACS analysis. Gates are based on secondary Ab-APC only for O4 staining and PE-conjugated isotype control for PDGFRα staining (Negative). Total O4$^+$ cells frequency (O4 & $^{++}$) is shown in parentheses.

FIG. 11A shows FACS plots showing pluripotency markers in an iPSC line grown on MEFs, and the lack of the same markers in cells at d81 of differentiation. FIG. 11B is a plot showing the more stringent gate used for sorting O4$^+$ cells before isolation and cryopreservation for the in vivo transplantations. FIG. 11C shows a brightfield image of O4$^+$ sorted cells plated after cryopreservation, during the recovery period of 48 hours. FIG. 11D shows live O4 staining in sorted OPCs, showing the retention of O4 and the proper ramified morphology.

FIG. 12A shows human PPMS iPSC-derived O4$^+$ OPCs transplanted into neonatal shiverer/rag2 mice. At 16 weeks, human cells exhibited dense engraftment in the corpus callosum (hNA, red). A large number had differentiated as MBP-expressing oligodendrocytes (green) and were distributed diffusely throughout corpus callosum. FIG. 12B is a confocal image showing co-localization of mouse axons (neurofilament; NF, red) and MBP$^+$ human oligodendrocytes (green). FIG. 12C and FIG. 12D show electron micrographs of myelinated axons exhibiting characteristic compact myelin with alternating major dense (arrowheads) and intraperiod lines. FIG. 12E shows that transplanted human cells retained progenitor characteristics with ~80% of hNA+ cells expressing OLIG2 (green; 16 weeks). FIG. 12F shows that at 16 weeks, individual NG2 cells had begun to migrate into the overlying cerebral cortex. FIG. 12G shows that iPSC-derived O4-sorted OPCs demonstrated limited bipotentiality in vivo: only a few GFAP$^+$ astrocytes were found in proximity to the lateral ventricle.

FIG. 13 shows demographic information of MS patients and healthy individuals from which iPSC lines have been derived.

FIG. 14A shows that fibroblasts with apparent changes in their morphology are visible at d3 of reprogramming. FIG. 14B shows transfection efficiency at d7, evaluated using nGFP mRNA. FIG. 14C shows iPSC-like colonies at d12. FIG. 14D shows an iPSC clone expanded in feeder-free conditions.

FIG. 15A shows nanostring analysis of 3 hESC lines, 2 fibroblasts lines, and 5 iPSC lines derived from MS patients or healthy controls; iPSC lines are indistinguishable from hESC lines. FIG. 15B shows that spontaneous embryoid body differentiation in vitro gives rise to cells from all germ layers. From left to right: AFP$^+$ endodermal cells, Tuji1$^+$ ectodermal cells, αSMA$^+$ mesodermal cells.

DETAILED DESCRIPTION OF THE INVENTION

Figure 2A:
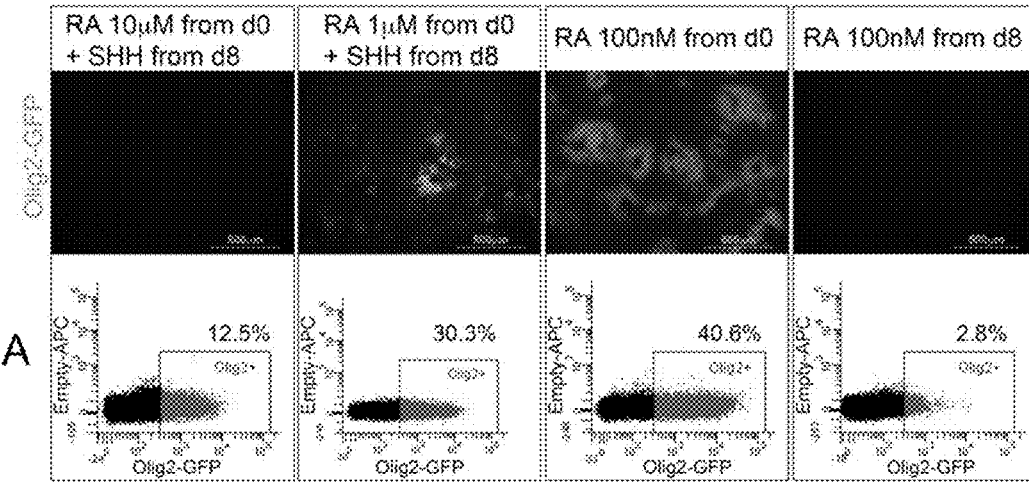
FIGS. 2A-2D show the requirement for RA and SHH to derive OLIG2$^+$ progenitor cells.

We developed a robust, fast, and reproducible differentiation protocol to generate human oligodendrocytes from PSCs using a chemically defined, growth factor-rich medium. Our protocol mimics oligodendrocyte differentiation during development. Within 8 days PSCs differentiate into PAX6$^+$ neural stem cells, which give rise to OLIG2$^+$ progenitors by day 12. OLIG2$^+$ cells become committed to the oligodendrocyte lineage by co-expressing NKX2.2 around day 18, and then differentiate to early OPCs by up-regulating SOX10 and PDGFRα around day 40. Late OPCs expressing the sulfated glycolipid antigen recognized by O4 antibody (O4$^+$) appear around day 50, and reach 40-70% of the cell population by 75 days of differentiation. O4$^+$ oligodendrocyte progenitor cells can be isolated by cell sorting for myelination studies, or can be terminally differentiated to mature MBP$^+$ oligodendrocytes. The timeline of our oligodendrocyte differentiation protocol is shown in FIG. 1.

The signaling pathways we manipulate to generate oligodendrocytes were selected based on knowledge gained from studies of rodent spinal cord embryonic development. Hu et al. (2009a). In vitro, RA and SHH signaling mimic the pMN environment, inducing differentiation of the PSCs to OLIG2 progenitor cells. In our cultures, SHH signaling is activated through a Smoothened agonist instead of the human recombinant SHH protein. We found that combining RA and SHH signaling with activin/nodal/TGFβ inhibition (through SB431542) and BMP4 inhibition (through LDN193189), generated the highest yield of OLIG2$^+$ progenitors. Due to the synergistic action of SB431542 and LDN193189, more than 70% of the cells express OLIG2 at day 12. This is a key difference between our protocol and that of Wang et al. (2013). Inhibition of both activin/nodal/TGFβ signaling and BMP signaling is also referred to as "dual SMAD inhibition."

There are several other important differences between our methods and previously published protocols. For example, we began neural induction with dual SMAD inhibition in adherent, as opposed to suspension, cultures. Wang et al. (2013); Hu et al. (2009b); Nistor et al. (2005). Using this approach, we started with only 10,000 cells/cm² at day 0, and yet achieved a great expansion of neural progenitors, and ultimately an abundant generation of OPCs. In addition, the optimal concentration of RA in our hands is found to be about 100 nM, which is one hundred times lower than the concentration used by other groups. Gil, J. E. et al., *FEBS Letters* 583:561-567 (2009); Izrael et al. (2007); Nistor et al. (2005). Further, induction with RA alone, without exogenous SHH, surprisingly generated a large population of OLIG2⁺ cells. We confirmed that an agonist of Smoothened is an efficient replacement for SHH and indeed showed superior efficacy in our hands (Stacpoole et al. 2013). Moreover, our invention, remarkably, is the first to show OLIG2 induction through RA in the absence of fibroblast growth factor (FGF) signaling. The combination of RA and FGF signaling is known to promote OLIG2 expression during chicken development and has been used for in vitro differentiation of both human ESCs and iPSCs. Pouya, A. et al., *PLoS One* 6:e27925 (2011); Nistor et al. (2005); Novitch, B. G. et al., *Neuron* 40:81-95 (2003). A recent study suggested that basic FGF (bFGF) is essential to the specification of oligodendrocytes of ventral forebrain origin, while it inhibits neuronal differentiation during the specification of oligodendrocytes from the spinal cord. Stacpoole et al. (2013). Nonetheless, we have achieved a high yield of OPCs in the absence of any exogenous FGF during our in vitro differentiation. Finally, the transition from adherent cultures to suspension cultures of cell spheres at day 12 proved to be a critical step to enrich the population of OLIG2⁺ cells and to restrict differentiation of our cultures to the oligodendrocyte lineage.

We also provide the first evidence that myelinating oligodendrocytes can be derived via reprogramming of PPMS-patient skin fibroblasts. The only previous report on MS-derived iPSCs showed that oligodendrocytes could be differentiated in vitro from an integrating, retrovirally reprogrammed iPSC line from a single, 35 years old, RRMS patient. Song, B., et al., *Stem Cell Res.* 8:259-273 (2012). We demonstrate in vivo myelination by OPCs derived from 4 integration-free iPSC lines from PPMS patients of both sexes and of ages of 50-62 years. Thus, the present invention differs from recent work using iPSC-derived OPCs in that our iPSC lines are derived from PPMS patients. Further, the cells used for in vivo transplantation have been sorted using the late OPC marker O4, to maximally restrict the differentiation potential. Despite these differences, PPMS-derived O4⁺-sorted OPCs exhibited similar engraftment efficiency, similar mitotic fraction and similar proportion of host ensheathed axons while generating fewer GFAP⁺ astrocytes compared to unsorted iPSC-derived OPCs reported previously. Taken together, our data show that PPMS-derived OPCs performed in vivo at least as efficiently as healthy iPSC-derived cells (Wang et al., 2013), and establish that our iPSC derivation and OPC induction protocols can generate myelinogenic oligodendrocytes from single-patient sample, which can be used in autologous cell-replacement therapies for MS.

A particular embodiment of the invention is a method of generating OLIG2+ OPCs by first preparing PSC colonies. PSCs are seeded (plated) at low density and grown in an adherent culture for about 1-2 days. "Low density" means about 8,000 to about 11,000 cells/cm². Cells are preferably seeded at about 9,500 to about 10,500 cells/cm², more preferably at about 10,000 cells/cm². After 1-2 days, the PSCs form colonies, which are preferably about 75 µm to about 300 µm in diameter, more preferably about 100 µm to about 250 µm in diameter.

The term "PSCs" has its usual meaning in the art, i.e., self-replicating cells that have the ability to develop into endoderm, ectoderm, and mesoderm cells. Preferably, PSCs are hPSCs. PSCs include ESCs and iPSCs, preferably hESCs and hiPSCs. PSCs can be seeded on a surface comprising a matrix, such as a gel or basement membrane matrix. A preferable matrix is the protein mixture secreted by Engelbreth-Holm-Swarm (EHS) mouse sarcoma cells, sold under trade names including MATRIGEL®, CULTREX®, and GELTREX®. Other suitable matrices include, without limitation, collagen, fibronectin, gelatin, laminin, poly-lysine, vitronectin, and combinations thereof.

The medium in which PSCs are cultured preferably comprises an inhibitor of rho-associated protein kinase (ROCK), for example, GSK269962, GSK429286, H-1152, HA-1077, RKI-1447, thiazovivin, Y-27632, or derivatives thereof.

The PSC colonies are then cultured in a monolayer to confluence in a medium comprising a low concentration of RA, at least one inhibitor of TGFβ signaling, and at least one inhibitor of BMP signaling, wherein the first day of culturing in this medium is day 0. A "low concentration of RA" is about 10 nM to about 250 nM. The concentration of RA is preferably about 10 nM to about 100 nM, or about 25 nM to about 100 nM, or about 20 nM, 30 nM, 40 nM, 50 nM, 60 nM, 70 nM, 80 nM, 90 nM, and preferably, about 100 nM or less. Inhibitors of TGFβ signaling include, for example, GW788388, LDN193189, LY2109761, LY2157299, and LY364947. A preferred inhibitor of TGFβ signaling is the small molecule SB431542. Inhibitors of BMP signaling include, for example, DMH1, dorsomorphin, K02288, and Noggin. A preferred inhibitor of BMP signaling is the small molecule LDN193189.

Cells reach confluence and express PAX6 at about day 8, at which point the confluent cells are cultured in a medium comprising SHH or an agonist of Smoothened, and a low concentration of RA. Agonists of Smoothened include, for example, SAG and purmorphamine. The SHH can be recombinant human SHH. Preferably, the medium lacks SHH. The transition from PSCs to OLIG2⁺ progenitors is associated with massive proliferation causing the cultures to become overconfluent, resulting in the cells forming three-dimensional structures, ideally by about day 12. "Overconfluent" means that the cells begin piling up on one another, such that not all cells are in complete contact with the culture surface, and some cells are not in contact with the culture surface at all, but are only in contact with other cells. Preferably, at least about 50%, 60%, or 70% of the overconfluent cells are OLIG2+ by about day 12.

If the OLIG2+ cells are to be further differentiated to O4+ cells, the overconfluent cells are lifted from the culture surface, which allows the formation of cell aggregates or spheres. OLIG2⁻ cells do not form aggregates, thus this process enriches for the OLIG2⁺ population, and OLIG2⁻ cells are eliminated gradually during subsequent media changes. For purposes of the present invention, the terms "aggregate" and "sphere" are used interchangeably and refer to a multicellular three-dimensional structure, preferably, but not necessarily, of at least about 100 cells.

Lifting can be performed mechanically, with a cell scraper or other suitable implement, or chemically. Chemical lifting can be achieved using a proteolytic enzyme, for example, collagenase, trypsin, trypsin-like proteinase, recombinant enzymes, such as that sold under the trade name TRYPLE naturally derived enzymes, such as that sold under the trade name ACCUTASE®, and combinations thereof. Chemical lifting can also be done using a chelator, such as EDTA, or a compound such as urea. Mechanical lifting or detachment offers the advantage of minimal cell death, however it produces aggregates of variable size, thus suitable spheres need to be selected through a manual picking process. Good spheres are defined as those having a round-shape, golden/brown color, with darker core and with a diameter between about 300 µm and about 800 µm. Detaching the cells using chemical methods, such as enzymatic digestion predominantly produces spheres that are appropriate for further culture. Therefore manual picking of spheres is not required, and the detachment steps can be adapted for automation and used in high throughput studies. However, enzymatic digestion increases cell death, resulting in a lower number of spheres.

We further provide a method of generating O4+ OPCs from OLIG2+ OPCs. Three-dimensional aggregates of OLIG2+ OPCs are cultured in suspension in a medium comprising a Smoothened agonist and a low concentration of RA for about 8 days. The OLIG2+ OPCs can be generated a method of the invention, for example, as described above, or by other methods known in the art. After about 8 days in the medium comprising the Smoothened agonist and RA, the medium is changed to one comprising PDGF, HGF, IGF-1, and NT3, and optionally, insulin (preferably about 10 µg/ml to about 50 µg/ml, more preferably about 25 µg/ml), T3 (preferably about 20 ng/ml to about 100 ng/ml, more preferably about 60 ng/ml), biotin (preferably about 50 ng/ml to about 150 ng/ml, more preferably about 100 ng/ml), and/or cAMP (preferably about 100 nM to about 5 µM, more preferably about 1 µM). The medium preferably lacks bFGF and epidermal growth factor (EGF). If OLIG2+ cells are generated by the method of the invention, culture in suspension preferably begins on about day 12, and culture in the medium comprising PDGF, HGF, IGF-1, and NT3 preferably begins on about day 20.

After about 10 days in suspension in the medium comprising PDGF, HGF, IGF-1, and NT3, the cell aggregates are plated in an adherent culture at a density of about 2 spheres/cm². (This is preferably at about day 30 where the method started on day 0 with PSCs cultured in a medium comprising RA, at least one inhibitor of TGFβ signaling, and at least one inhibitor of BMP signaling.) The surface on which the cell aggregates are plated and cultured can comprise an extracellular matrix protein (e.g., collagen, fibronectin, laminin) and/or a positively charged poly-amino acid (e.g., poly-arginine, poly-lysine, poly-ornithine). Preferably the surface comprises laminin and/or poly-ornithine.

Upon plating the cell aggregates, the medium comprising PDGF, HGF, IGF-1, and NT3 can be continued (Option A), or a medium comprising AA and lacking growth factors (e.g., PDGF, HGF, IGF-1, NT3, bFGF, and/or EGF) can be used (Option B). The medium comprising AA can optionally comprise insulin, T3, biotin, and/or cAMP. Cells cultured in the medium comprising PDGF, HGF, IGF-1, and NT3 are optimally O4+ by about 45 days after plating. Preferably, at least about 35%, 40%, 45%, 50%, 55%, 60%, 65%, 70%, 75%, or 80% of these cells are O4+ by about 45 days after plating (day 75). Cells cultured in the medium comprising AA are optimally O4+ by about 25 days after plating. Preferably, at least about 20%, 25%, 30%, 35%, or 40% of these cells are O4+ by about 25 days after plating (day 55). Preferably, at least about 30%, 35%, 40%, 45%, 50%, 55%, or 60% of these cells are O4+ by about 33 days after plating (day 63). Preferably, at least about 35%, 40%, 45%, 50%, 55%, 60%, 65%, 70%, or 75% of these cells are O4+ by about 45 days after plating (day 75).

Mature oligodendrocytes expressing myelin basic protein can be generated by culturing the O4+ OPCs in the absence of PDGF, HGF, IGF-1, and NT3 for about three weeks, until cells are MBP+. Preferably, at least about 20%, 25%, 30%, 35%, 40%, or 45% of the O4+ OPCs are MBP+ after about 20 days in culture in the medium lacking PDGF, HGF, IGF-1, and NT3. This occurs on about day 95 for "Option A" cells, and on about day 60 for "Option B" cells. Culturing "Option B" cells until at least about day 75 results in a higher efficiency of MBP+ expressing cells.

The invention also encompasses OPCs, oligodendrocytes, and myelin-producing cells generated by the methods of the invention, and non-human mammals comprising them, preferably mice and/or rats. A myelin-producing cell is any cell that produces myelin, including without limitation, oligodendrocytes. In some embodiments, myelin-producing cells are differentiated from PSCs, and in such embodiments, the PSCs can be iPSCs. The iPSCs can be derived from a somatic cell of a subject. In one aspect, the subject has a demyelinating or dysmylelinating disease or disorder.

In one aspect, the invention provides a method for generating viral and integration-free iPSCs from patients with MS, particularly PPMS. Our differentiation protocol can be used for the efficient differentiation of such iPSCs to OPCs and functional oligodendrocytes, as demonstrated by in vivo myelination in the shiverer mouse.

The invention also provides a model system for a neurological disease, preferably a demyelinating or dysmyelinating disease or disorder. In one aspect, the model system comprises a myelin-producing cell differentiated from an iPSC derived from a subject having a demyelinating or dysmyelinating condition. The model system can further comprise a non-human mammal into which the myelin-producing cell has been transplanted. In one embodiment, the non-human mammal is a mouse or a rat. Model systems provided by the invention can be used to study demyelinating or dysmyelinating diseases or disorders, including understanding underlying mechanisms and defining therapeutic targets.

The invention also provides methods for treating and/or preventing a neurological disease or disorder in a subject by generating OPCs or oligodendrocytes according to a method of the invention; and administering an effective amount of the cells to the subject. Once transplanted, the oligodendrocytes, or OPCs that have differentiated to oligodendrocytes in vivo, promote myelinogenesis in the nervous system of the subject. Thus, the invention provides a use of the OPCs or oligodendrocytes of the invention in the treatment and/or prevention of a neurological disease or disorder in a subject. The neurological disease or disorder can be a demyelinating or dysmyelinating disease, or a neurodegenerative disease. The neurological disease or disorder can affect the central nervous system, the peripheral nervous system, or both. In some embodiments, the demyelinating or dysmyleinating disease is an inflammatory demyelinating disease (such as multiple sclerosis, optic neuritis, Devic disease, acute-disseminated encephalomyelitis and transverse myelitis), viral demyelination, demyelination caused by acquired metabolic disorders, leukodystrophies (including hypomyelinating diseases, such as Pelizaeus-Merzbacher Disease and hereditary spastic paraplegia), X-linked disorders of proteo-lipid protein production, metabolic demyelinations and lysosomal storage disorders (such as metachromatic leukodystrophy-MLD, Tay-Sachs, Sandhoff's and Krabbe's diseases), vanishing white matter disease, and periventricular leukomalacia. MS and particularly PPMS are also conditions that can be treated or prevented by the methods of the invention. In a preferred embodiment, the OPCs or oligodendrocytes generated by a method of the invention are derived from iPSCs generated from a somatic cell of the subject.

Alongside its potential for autologous cell transplantation, iPSC technology is emerging as a tool for developing new drugs and gaining insight into disease pathogenesis. Han, S. S. W. et al., *Neuron.* 70:626-644 (2011). The methods and cells of the invention will aid the development of high-throughput in vitro screens for compounds that promote myelination. Lee, S. et al., *Nat Protoc.* 8:771-782 (2013). To that end, we provide a method of identifying a compound that promotes myelination, the method comprising generating myelin-producing cell by a method of the invention; contacting the myelin-producing cell with a candidate compound; and determining whether the candidate compound promotes neuron myelination. In one embodiment, the compound is a candidate therapeutic agent for treating a neurological disease or disorder, such as a demyelinating or dysmyelinating condition, and the method includes determining whether the candidate therapeutic agent has a beneficial effect on neuron myelination, wherein such beneficial effect is indicative of a candidate therapeutic agent for treating a demyelinating or dysmyelinating disease or disorder. The beneficial effect can be, for example, prevention of neuron demyelination, reduction of neuron demyelination, increased neuron conductance, and/or enhanced neuron myelination. Preferably, the method is conducted in a high-throughput format.

Figure 16:
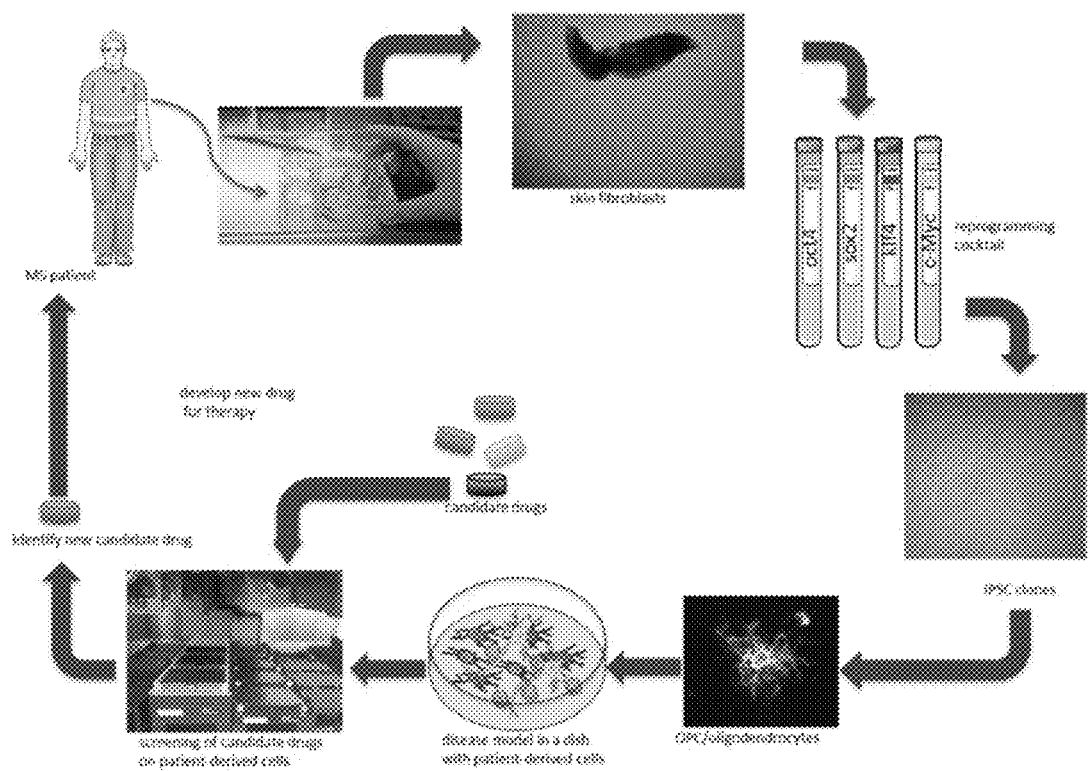
FIG. 16 shows an approach to understanding multiple sclerosis.

The cells, systems, and methods of the invention can also be useful for studying neurological diseases. In particular, the PPMS iPSC lines described here provide a new resource to investigate the process of neurodegeneration, particularly in MS (FIG. 16).

As used in this specification and the appended claims, the singular forms "a," "an," and "the" include plural referents, unless the context clearly dictates otherwise. The terms "a" (or "an"), as well as the terms "one or more," and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Unless defined otherwise, all technical and scientific terms used herein have the same meaning as commonly understood by one of ordinary skill in the art to which this invention is related. For example, *The Dictionary of Cell and Molecular Biology* (5th ed. J. M. Lackie ed., 2013), the *Oxford Dictionary of Biochemistry and Molecular Biology* (2d ed. R. Cammack et al. eds., 2008), and *The Concise Dictionary of Biomedicine and Molecular Biology*, P-S. Juo (2d ed. 2002) can provide one of skill with general definitions of some terms used herein.

Units, prefixes, and symbols are denoted in their Systeme International de Unites (SI) accepted form. Numeric ranges are inclusive of the numbers defining the range. The headings provided herein are not limitations of the various aspects or embodiments of the invention, which can be had by reference to the specification as a whole. Accordingly, the terms defined immediately below are more fully defined by reference to the specification in its entirety.

Wherever embodiments are described with the language "comprising," otherwise analogous embodiments described in terms of "consisting of" and/or "consisting essentially of" are included.

By "subject" or "individual" or "patient" is meant any subject, particularly a mammalian subject, for whom diagnosis, prognosis, or therapy is desired. Mammalian subjects include humans, domestic animals, farm animals, sports animals, and zoo animals including, e.g., humans, non-human primates, dogs, cats, guinea pigs, rabbits, rats, mice, horses, cattle, pigs, and so on.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already with the disorder. In certain embodiments, a subject is successfully "treated" for a neurological disease or disorder, particularly a demyelinating or dysmyelinating disease or disorder, according to the methods provided herein if the patient shows, e.g., total, partial, or transient alleviation or elimination of symptoms associated with the disease or disorder.

"Prevent" or "prevention" refers to prophylactic or preventative measures that prevent and/or slow the development of a targeted pathologic condition or disorder. Thus, those in need of prevention include those prone or susceptible to the disease or disorder. In certain embodiments, a neurological disease or disorder, particularly a demyelinating or dysmyelinating disease or disorder, is successfully prevented according to the methods provided herein if the patient develops, transiently or permanently, e.g., fewer or less severe symptoms associated with the disease or disorder, or a later onset of symptoms associated with the disease or disorder, than a patient who has not been subject to the methods of the invention.

The invention is further described in the following non-limiting Examples.

EXAMPLES

Example 1

Differentiation of Oligodendrocytes from hESC Lines

Figure 2B:
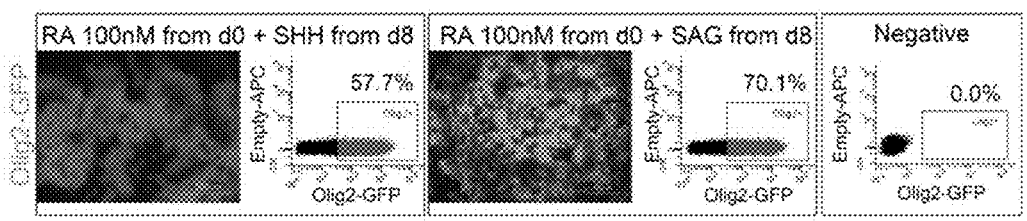
Figure 3A:
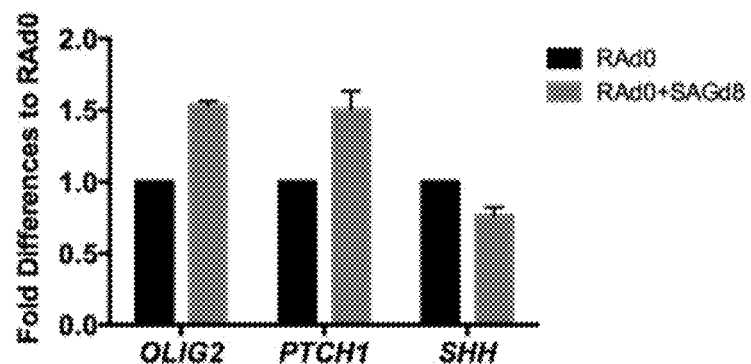
FIGS. 3A-3C show SHH and dual SMAD inhibition requirements for OLIG2$^+$ progenitors.
Figure 3B:
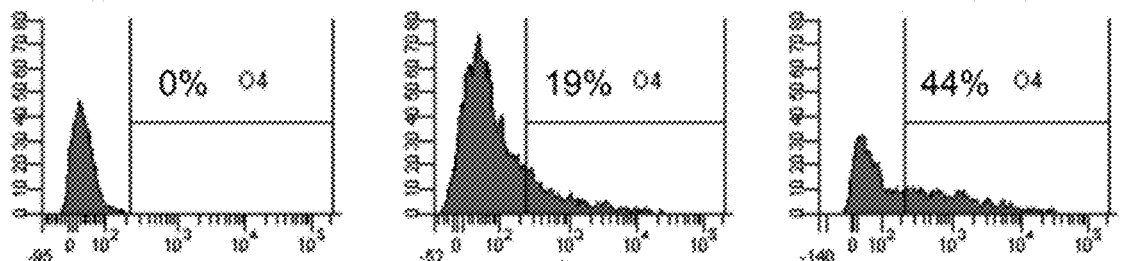
Figure 3C:
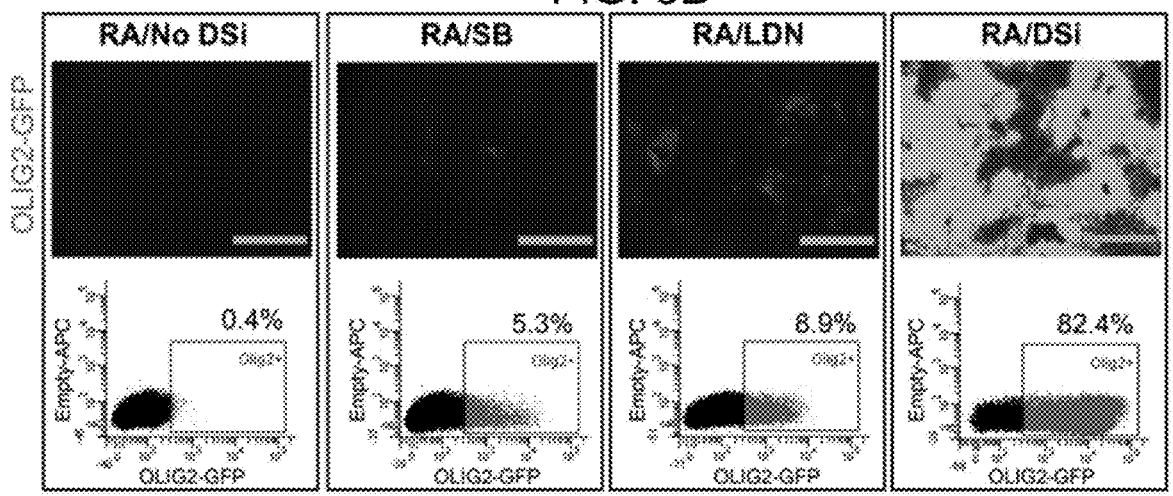

We used an OLIG2-GFP knock-in hESC reporter line (Liu et al., 2011) to track OLIG2$^+$ progenitors by live fluorescent imaging. First, we induced PAX6$^+$ cells using dual inhibition of SMAD signaling in adherent cultures. Chambers, S. M. et al., *Nat Biotechnol.* 27:275-80 (2009). Next, to mimic the embryonic spinal cord environment, we applied different concentrations of RA and/or SHH at various times and quantified OLIG2-GFP expression through flow cytometry (FIG. 2A). Application of 100 nM RA from the beginning of induction generated 40.6% of OLIG2$^+$ progenitors, whereas addition of SHH at 100 ng/ml from day 8 increased the yield to 57.7% (FIG. 2B). Interestingly, cells without exogenous SHH during the first 12 days, showed an upregulation of SHH mRNA (FIG. 3A) and differentiated to O4$^+$ cells, although at lower efficiency compared to cells treated with SHH (FIG. 3B).

Figure 2C:
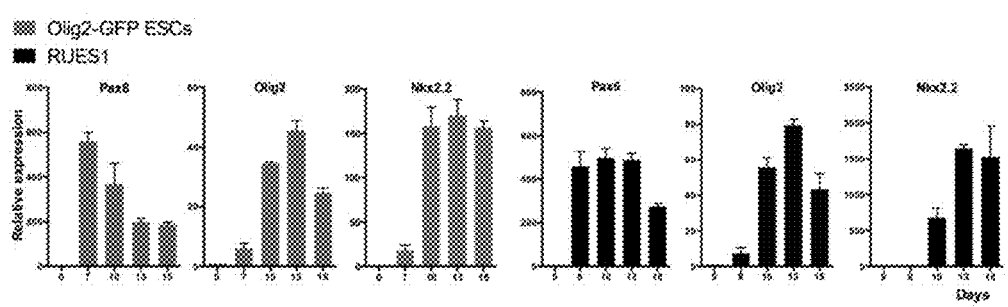

We then replaced the recombinant human SHH protein with SAG, which increased the yield further to 70.1% OLIG2$^+$ progenitors (FIG. 2B). At day 12, cells were detached and placed into low-attachment plates to promote their aggregation into spheres. The minimum number of cells required to form a sphere was at least 100 cells, and we noted that the majority of cells in the spheres were GFP⁺. To investigate this further, we sorted day 12 cultures for GFP, and observed that only the GFP⁺ cells formed aggregates (FIG. 2C). This suggests that the aggregation step alone provides enrichment for the OLIG2⁺ population.

Figure 2D:
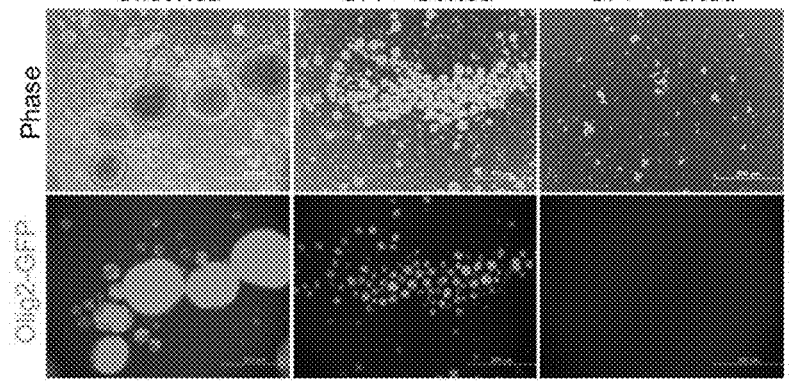
Figure 4A:
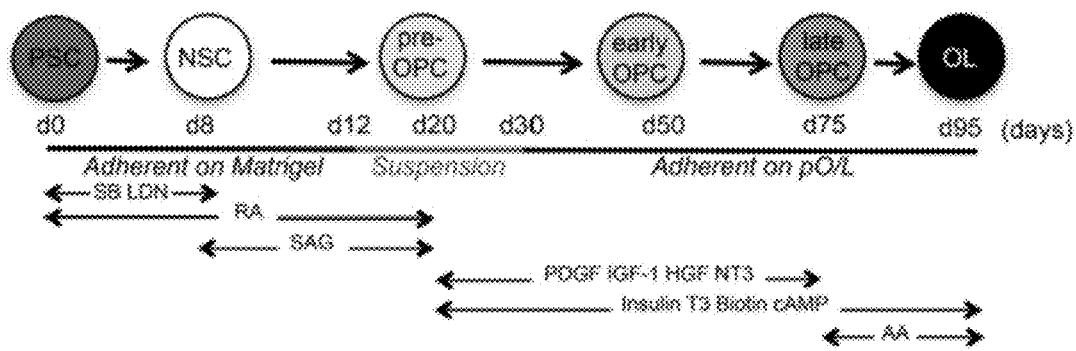
FIGS. 4A-4M show generation of oligodendrocytes from human pluripotent stem cells.
Figures 4B, 4C, 4D, 4E, 4F, 4G, 4H, 4I, 4J, 4K, 4L, 4M:
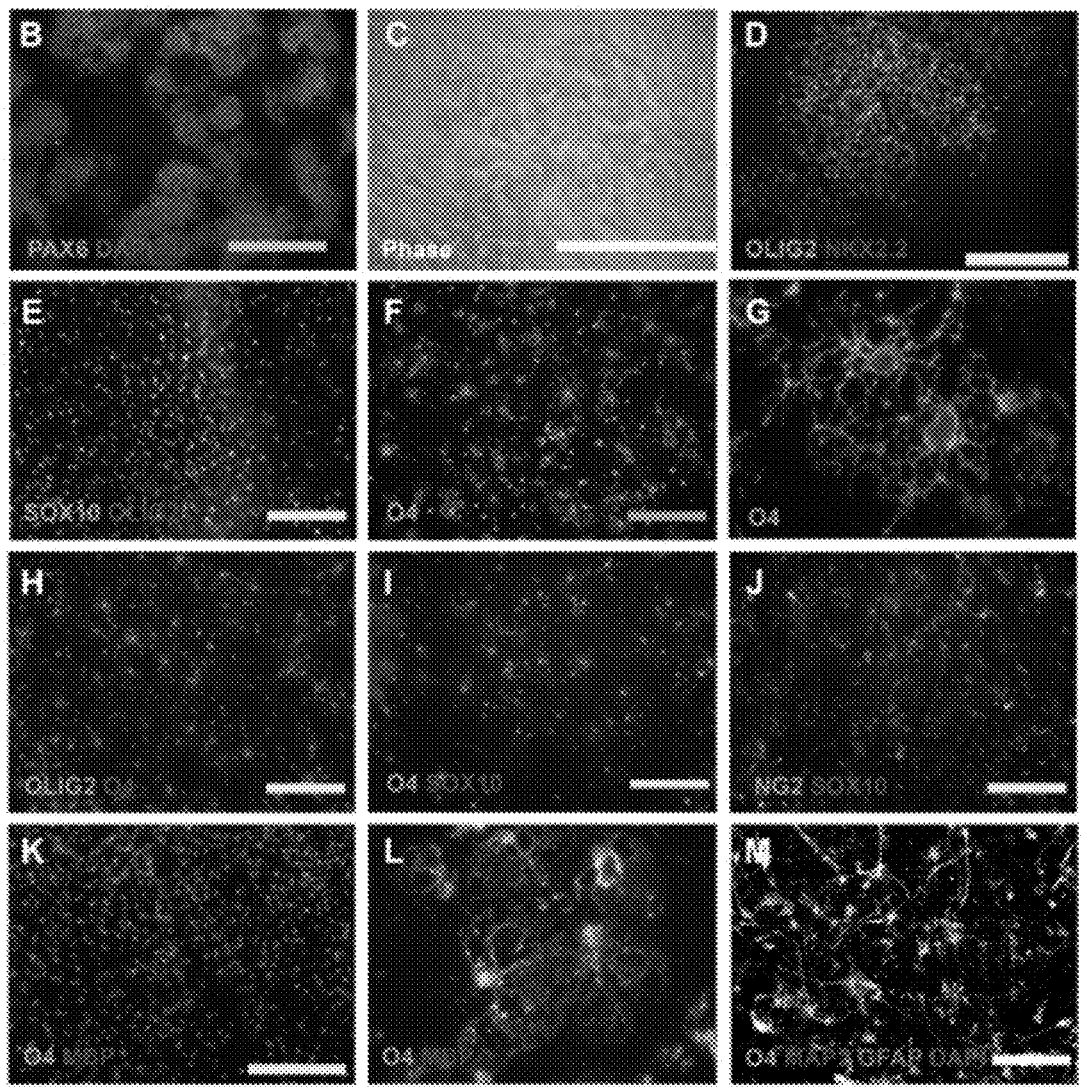

Next, we validated the initial steps towards the generation of OLIG2⁺ progenitors by differentiating a second hESC line (RUES1), and comparing the transcript levels of PAX6, OLIG2, and NKX2.2 by qRT-PCR. The upregulation of these transcription factors followed a similar temporal pattern to that of the OLIG2-GFP line, with PAX6 induction around day 7, OLIG2 peak around day 13, and sustainably high levels of NKX2.2 after day 10 (FIG. 2D). Based on these results, we used the non-genetically modified RUES1 line to develop the following steps of the protocol, from OLIG2⁺ progenitors to MBP⁺ mature oligodendrocytes (FIG. 4A). PAX6⁺ cells arose at day 7, and by day 12 they arranged into multilayered structures (FIG. 4B, FIG. 4C). From day 12 to day 30, cells were grown as spheres and then plated onto poly-L-ornithine/laminin (pO/L)-coated dishes for the remainder of the protocol.

To promote maturation toward the O4⁺ stage, PDGF-AA, HGF, IGF1, and NT3 were added to the culture medium from day 20 onward. OLIG2⁺ progenitors upregulated NKX2.2, then SOX10, and finally matured to late OPCs identified by O4 live staining, and by their highly ramified processes (FIG. 4D-FIG. 4G). O4⁺ OPCs expressing OLIG2, SOX10 and NG2 (FIG. 4H-FIG. 4J), appeared as early as day 50 and their numbers increased dramatically around day 75. During the differentiation, 40-50% of progenitor cells were proliferative, as indicated by Ki67 staining. However, the highly ramified O4⁺ cells did not divide in vitro (FIG. 5A-FIG. 5C). Additionally, 34±4% of O4⁺ OPCs differentiated into MBP⁺ mature oligodendrocytes after growth-factor withdrawal from the medium for at least two weeks (FIG. 4K-FIG. 4L, FIG. 5D). These cultures also consisted of other cell-types, namely 15±2% GFAP⁺ astrocytes and 20±2% MAP2⁺ neurons of total cells respectively (FIG. 4M, FIG. 5E).

We also used an alternative strategy to generate approximately 30% O4⁺ cells after only 55 days of culture, significantly reducing the length and costs of differentiation. The mitogens PDGF, NT3, IGF-1 and HGF were withdrawn from the medium as early as at day 30, when the selected spheres were seeded. This resulted in the appearance of O4⁺ cells at day 55. The cultures were continued to increase the frequency of O4⁺ cells to levels comparable to the longer protocol (FIG. 6).

As shown in Table 1, O4 efficiencies ranged from 28% to 80% with nine different PSC lines, and the average was greater than 60% in four lines. Cells were stained with O4 antibody and analyzed by flow cytometry. One hESC line (RUES') and eight hiPSC lines were tested. Technical replicates were performed using different batches of each line, at different passages. Results are also expressed as mean percentages ±SEM.

TABLE 1

Percentages of O4⁺ OPCs after ~75 Days of Differentiation

| Cell line | N | O4⁺(%) | Mean ± SEM (%) |
|---|---|---|---|
| 102 | 4 | 40, 71, 72, 74 | 61.8 ± 7.6 |
| 104 | 4 | 55, 61, 61, 68 | 61.3 ± 2.7 |
| 107 | 1 | 48 | |
| 109 | 3 | 55, 60, 70 | 61.7 ± 4.2 |
| 110 | 3 | 29, 37, 73 | 46.2 ± 13.7 |
| 111 | 2 | 46, 47 | 46.4 ± 0.4 |
| 130 | 4 | 43, 47, 58, 76 | 56.1 ± 7.2 |
| 197 | 1 | 28 | |
| RUES1 | 5 | 36, 54, 68, 78, 80 | 62.9 ± 8.2 |

N = Number of Technical Repeats

Figures 7A, 7B, 7C, 7D, 7E, 7F, 7G, 7H, 7I:
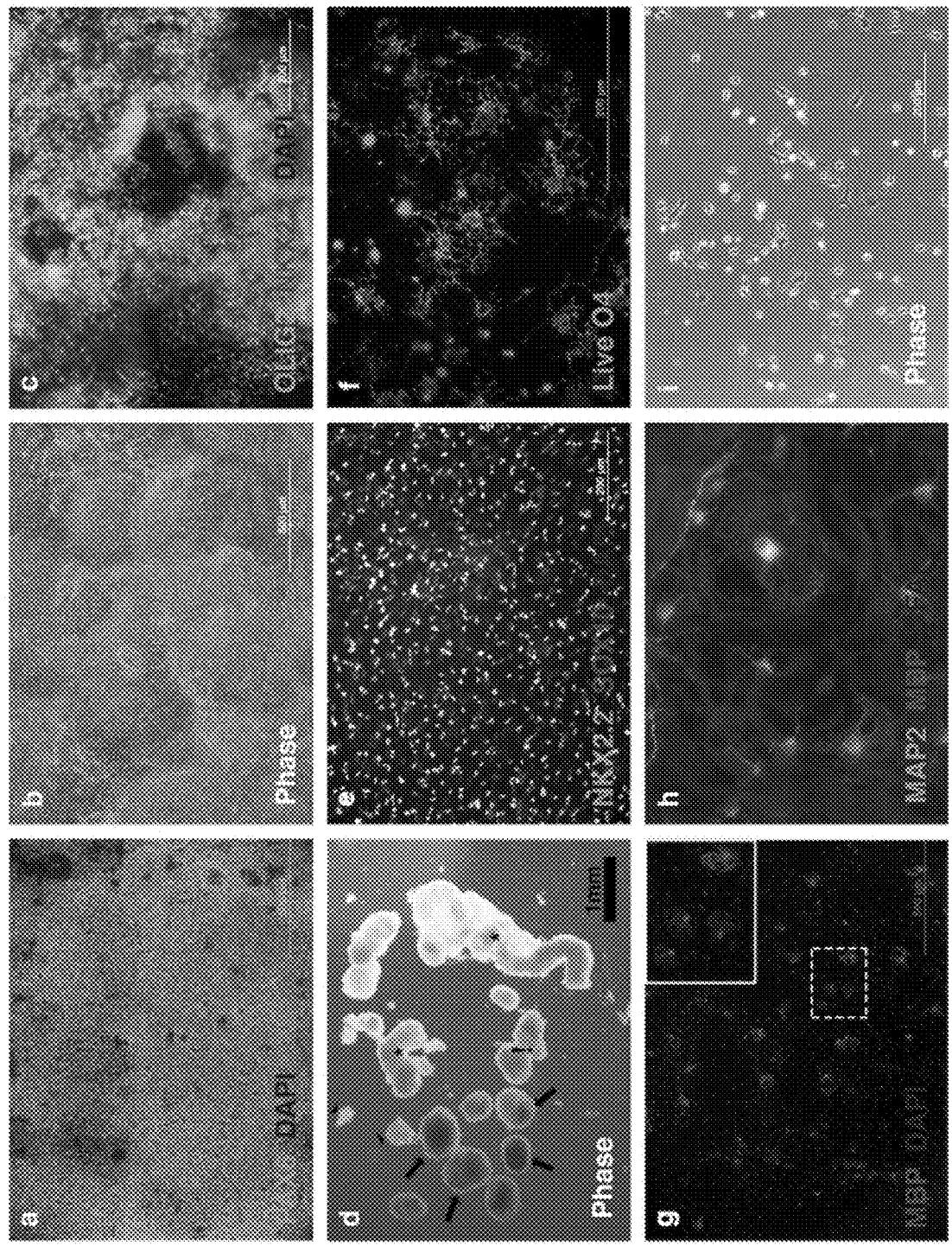
FIGS. 7A-7I show the fundamental steps of hPSC differentiation to oligodendrocytes.

In both strategies, the withdrawal of the mitogens drives the terminal differentiation of OPCs to oligodendrocytes expressing MBP, although MBP⁺ cells do not align with axon fibers under these culture conditions (FIG. 7G, FIG. 7H). For myelination studies, O4⁺ OPCs can be purified through fluorescent activated cell sorting (FACS) and transplanted in vivo. O4⁺ cells can also be cryopreserved immediately after sorting and thawed 24-48 hours prior to transplantation.

As described above, at various stages of the protocol, cultures were checked for the expression of appropriate markers by either qRT-PCR or immunofluorescence. When performing immunofluorescent analysis of the cultures at day 8 for PAX6 (FIG. 7A) and at day 12 for OLIG2 and NKX2.2 (FIG. 7C), the frequencies should be greater than 90% for the PAX6⁺, 70% for the OLIG2⁺, and 30% for the OLIG2⁺/NKX2.2⁺ cells. By day 40-50, SOX10 should be expressed and should co-localize with OLIG2 and NKX2.2 (FIG. 7E). From day 50 to 75, live O4 staining can be performed to detect the appearance of O4⁺ cells and their expansion (FIG. 6A-FIG. 6F, FIG. 7F). In human development, OPCs are characterized by PDGFRα and NG2 expression, followed by expression of O4. Jakovcevski, I. et al., Front Neuroanat 3:5 (2009). Under our culture conditions, by day 75, most O4⁺ cells have lost PDGFRα but have retained NG2 expression. At this stage we did not observe any residual pluripotent cells in culture.

Finally, O4⁺ cells can either be isolated via FACS or further differentiated to MBP⁺ oligodendrocytes (FIG. 7G, FIG. 7H). Other cell-types also exist in day 75 cultures, although at lower percentages. We generally find GFAP⁺ cells in about 15% of the total cell population and about 20% βIII-Tubulin⁺ cells (FIG. 7H). After the final differentiation step, when cells are cultured in Glial Medium for 2 weeks, about 35% of the O4⁺ cells should also express MBP.

Example 2

Differentiation of Oligodendrocytes from PPMS-iPSC Lines

To show that our protocol can be applied to iPSC lines, we obtained skin biopsies from four PPMS patients. Fibroblast cultures were established from the biopsies, and iPSCs were generated using daily transfections with a cocktail of modified mRNAs, (Warren et al., Cell Stem Cell. 7:618-30 (2010)), together with a cluster of miRNAs to improve the reprogramming efficiency for the most refractory lines (Stemgent). From day 12 to day 15 of reprogramming, TRA-1-60⁺ colonies (FIG. 8A) were identified by live staining, picked, expanded, and characterized by immunofluorescence for pluripotency markers (FIG. 8B).

Figures 9A, 9B, 9C:
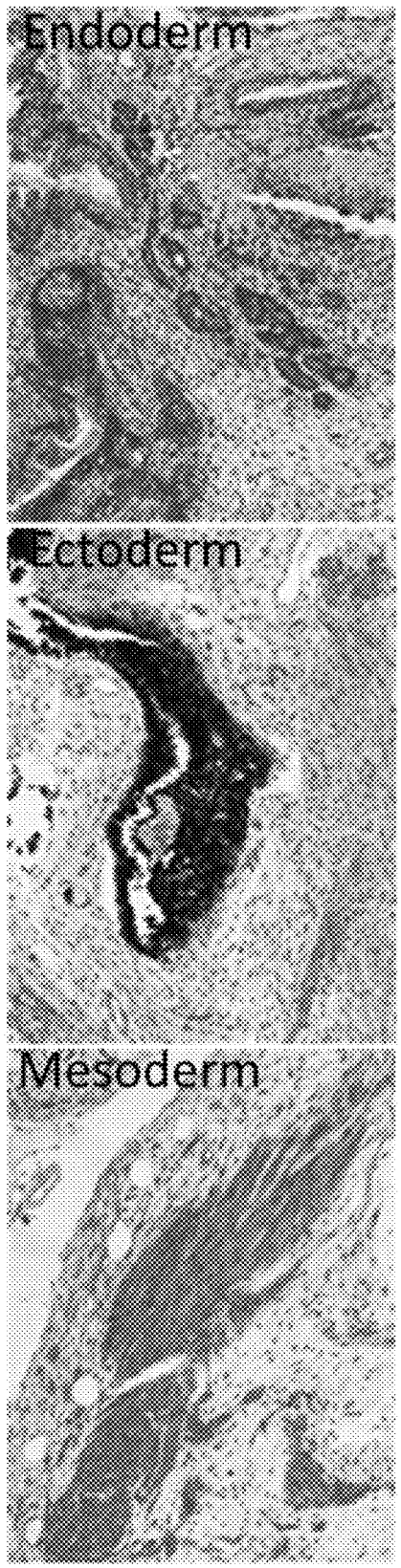
FIGS. 9A-9C show characterization of teratoma formation in iPSC lines. Representative pictures from endoderm (FIG. 9A), ectoderm (FIG. 9B), and mesoderm (FIG. 9C) of teratoma formation in vivo after transplantation of cells from iPSC line 102 into immunodeficient mouse.

Expression profiling for seven pluripotency genes confirmed that all four iPSC lines exhibited a profile comparable to a reference hESC line and divergent from the parental fibroblasts (FIG. 8C). All iPSC lines displayed a normal karyotype (FIG. 8D) and were able to differentiate into cell types of the three germ layers, both in vitro, via spontaneous embryoid body differentiation (FIG. 8E), and in vivo via teratoma assay (FIG. 8F; FIG. 9).

Figures 10A, 10B, 10C, 10D, 10E, 10F, 10G, 10H, 10I:
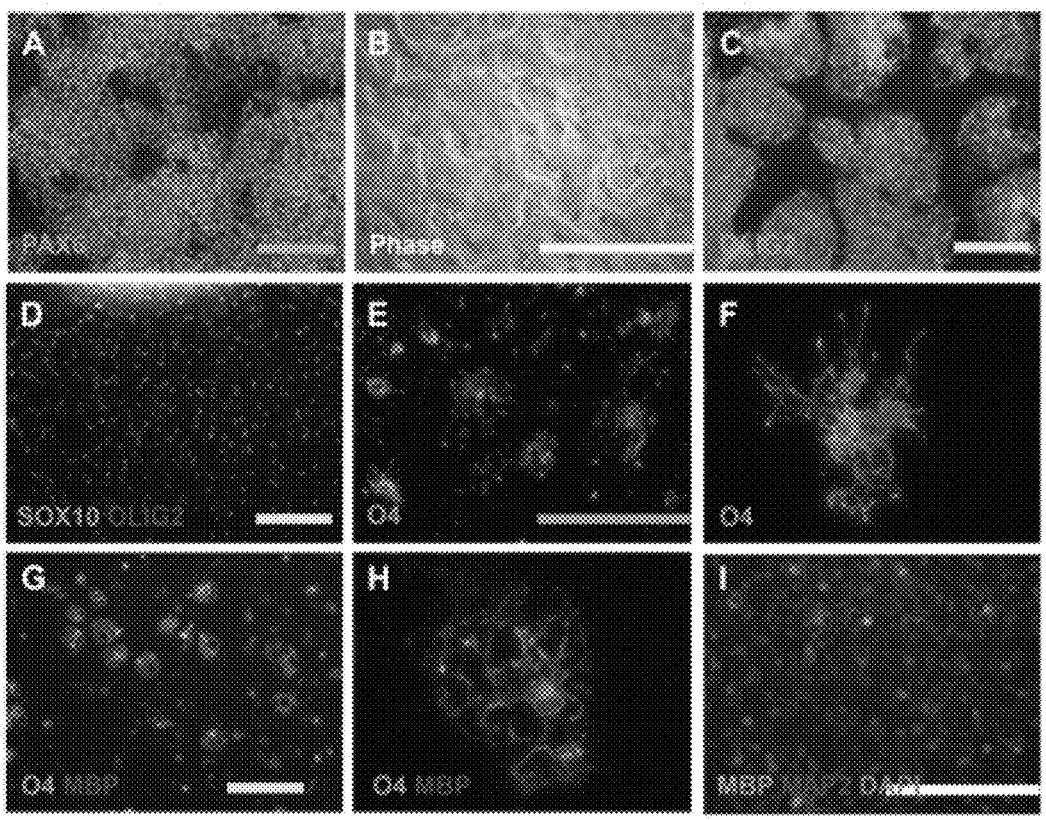
FIGS. 10A-10J show that PPMS-iPSCs generate OPCs and mature oligodendrocytes in vitro.
Figure 10J:
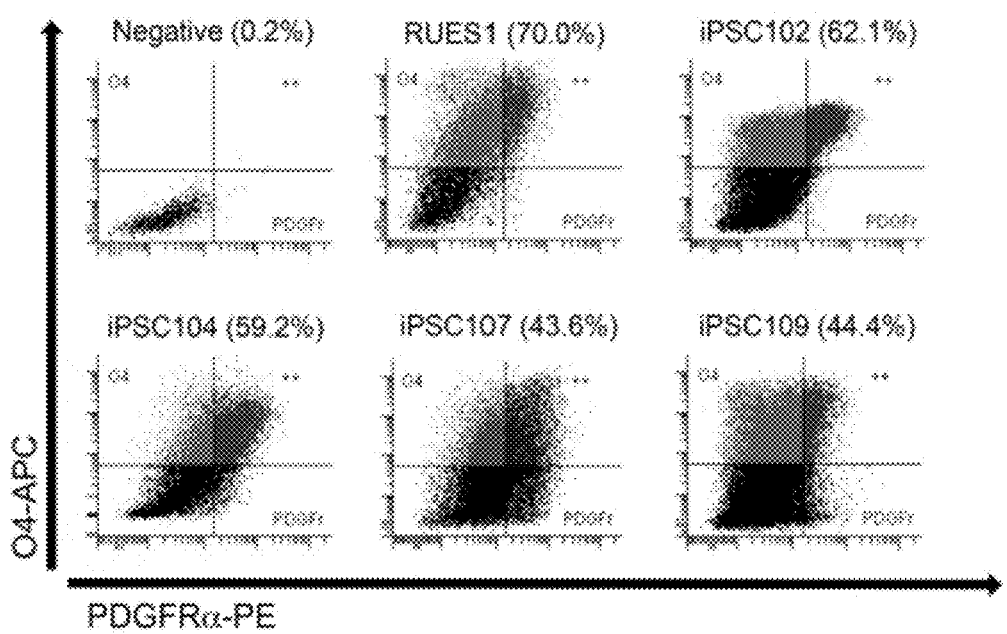

Next, we assessed whether the protocol was reproducible with our PPMS-iPSC lines. All iPSC lines tested were found to perform similarly to the RUES1 line (FIG. 10A-FIG. 10I). The protocol was greatly reproducible and highly efficient, as calculated by the frequency of sorted O4$^+$ OPCs, with up to 70% O4$^+$ cells from RUES1, and 43.6%-62.1% from the PPMS iPSC lines. Additionally, we found that the O4$^+$ fraction contains a subpopulation of cells double positive with PDGFRα (FIG. 10J). O4$^+$ cells could be easily purified by fluorescent activated cell sorting (FACS), frozen and thawed, without losing their morphology (FIG. 11D).

Example 3

Axon Myelinate Mouse Brain by PPMS-Derived Late OPCS

Figure 11A:
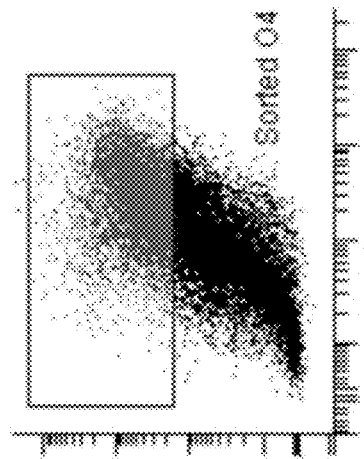
FIGS. 11A-11D shows characterization of cells before transplantation for the in vivo studies.
Figure 11B:
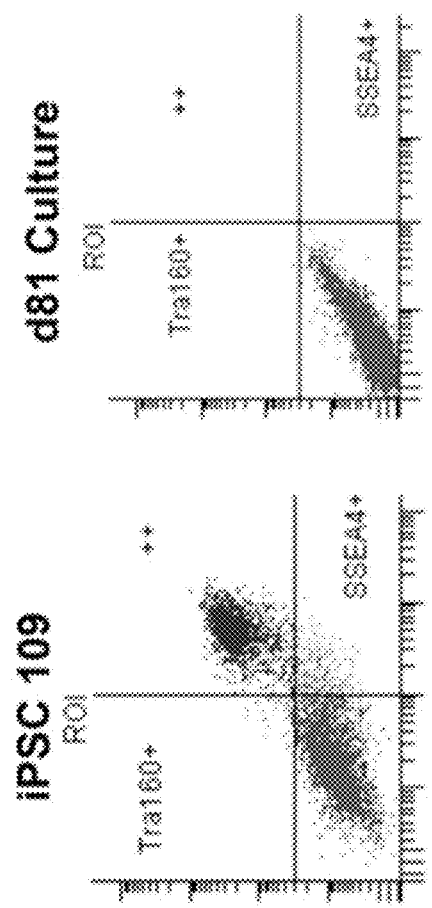
Figure 11D:
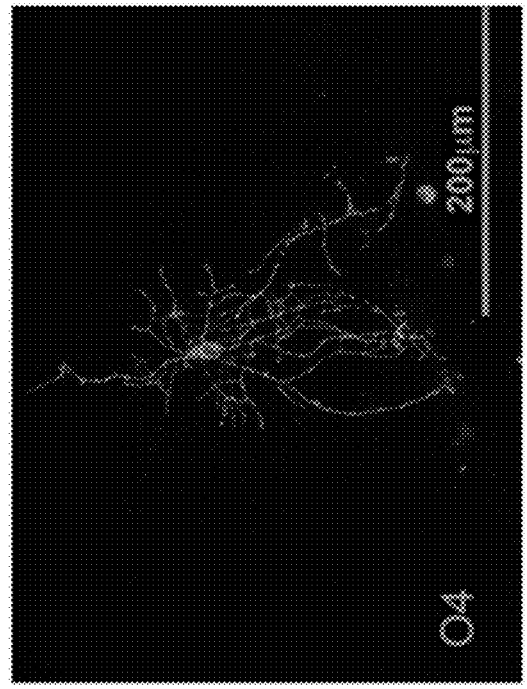
Figure 11C:
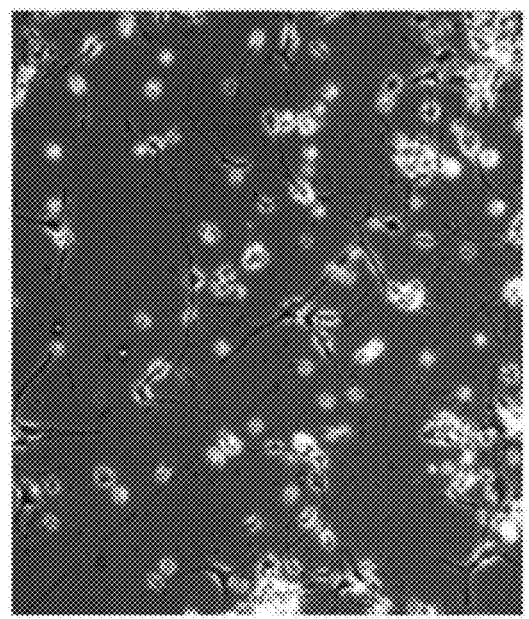
Figures 12A, 12B, 12C, 12D, 12E, 12F, 12G:
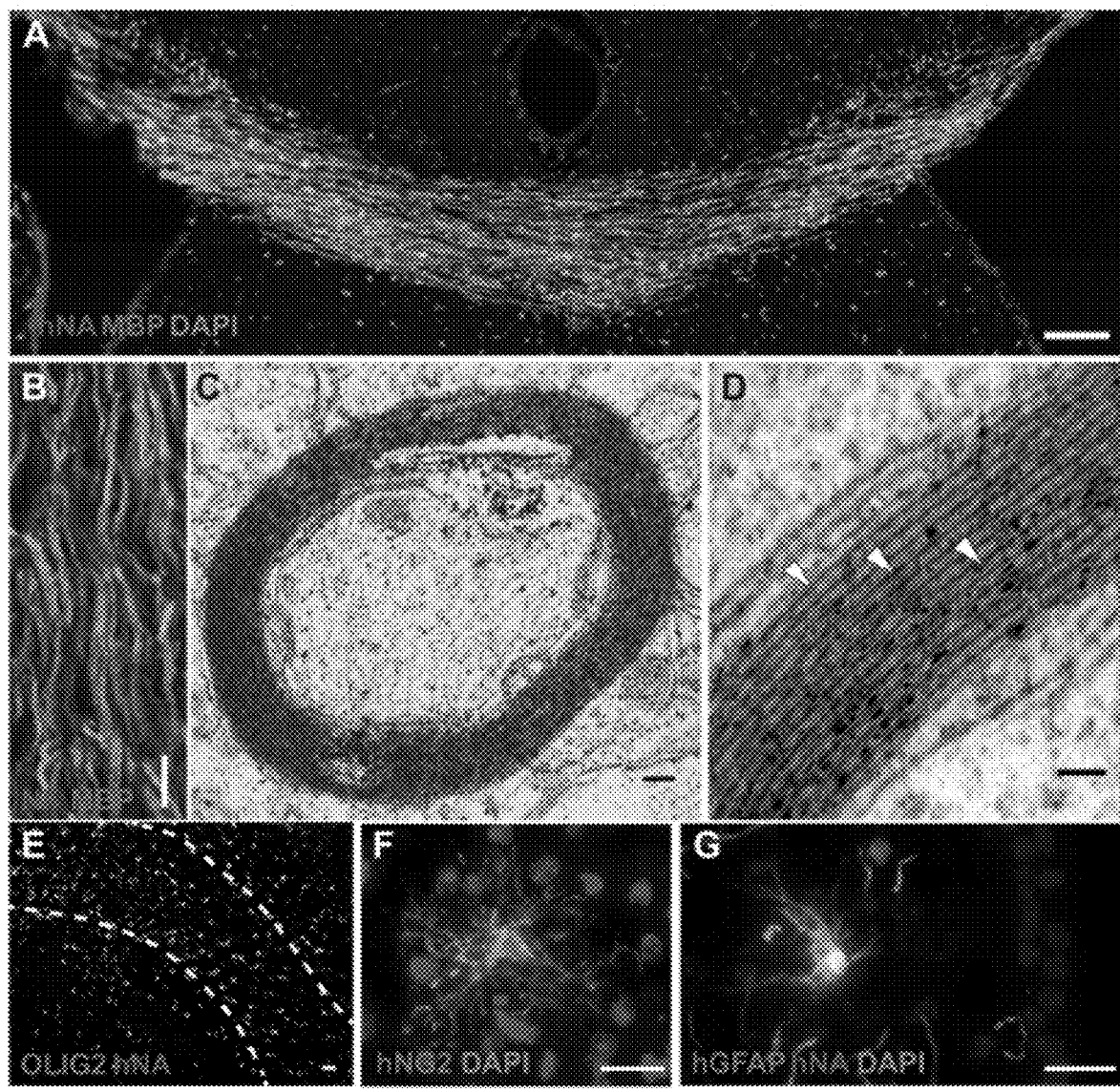
FIGS. 12A-12G show PPMS-derived OPCs engraft and differentiate to myelinogenic oligodendrocytes in vivo.

To verify that OPCs obtained through our protocol were functionally myelinogenic, we injected day 75 FACS-purified O4$^+$ cells ($10^5$ cells/animal) into the forebrain of neonatal, immunocompromised shiverer mice (FIG. 11A). The injected cells were depleted of any contaminant iPSCs, as shown by flow cytometry analysis of pluripotency markers SSEA4 and TRA-1-60 (FIG. 11B). However, we purified our cultures before in vivo transplantation to retain the potential for translation to clinical studies. Cells were frozen, thawed, and allowed to recover for 24-48 hours before transplantation (FIG. 11C). Animals were sacrificed at 12-16 weeks, at which point human hNA$^+$ cells were distributed throughout the corpus callosum and forebrain white matter. The density of hNA$^+$ cells in the corpus callosum at 12 weeks was 34,400±3,090 cells/mm$^3$, and by 16 weeks, the number of human cells had approximately doubled since 12 weeks. We did not observe the presence of cell clusters or overt tumorigenesis, and the proliferative fraction of engrafted hNA$^+$ cells was 17% at 12 weeks, and decreased to only 8% Ki67$^+$ at 16 weeks when only 5% of cells were PCNA$^+$. Importantly, more than 80% of hNA$^+$ cells in the corpus callosum co-expressed OLIG2 protein, suggesting that the engrafted cells were restricted to the oligodendrocyte lineage (FIG. 12E). Furthermore, human MBP$^+$ oligodendrocytes were found diffusely throughout engrafted corpus callosum at 12 and 16 weeks (FIG. 12A). At 16 weeks, 31±3% of host mouse axons were ensheathed within the engrafted mouse corpus callosum (FIG. 12B).

Transmission electron microscopy on 16 week-old corpus callosum revealed mature compact myelin with the presence of alternating major dense and intraperiod lines (FIG. 12C, FIG. 12D); while uninjected shiverer/rag2 mice possessed thin and loosely wrapped myelin. Likewise, the thickness of myelin ensheathment, as assessed by g-ratio measurement, reflected a restoration of normal myelin in several callosal axons.

At 12 weeks, transplanted hNA$^+$ cells remained as NG2$^+$ OPCs in the corpus callosum (FIG. 12E), and by 16 weeks they started to migrate to the overlying cerebral cortex (FIG. 12F). Very few O4-sorted cells underwent differentiation as hGFAP$^+$ astrocytes, and the majority of hGFAP$^+$ cells were localized to the SVZ and around the ventricles (FIG. 12G), suggesting that the local environment may induce astrocytic differentiation in these regions. Similarly, hNESTIN-expressing cells were rarely found in corpus callosum and likewise concentrated in SVZ. Importantly, βIII-Tubulin$^+$ neurons were not detected in any of the engrafted animals. Taken together, our data demonstrate that PPMS-derived O4-sorted cells were capable of mature oligodendrocyte differentiation in vivo and the formation of dense compact myelin resembling normal myelin in the brain.

Example 4

Detailed Experimental Procedures for Examples 1-3

Cell Lines

Three hESC lines and 4 hiPSC lines were used. RUES1 and HUES 45 are both NIH-approved hESC lines; OLIG2-GFP reporter line is derived from BG01 hESC line (University of Texas Health Science Center at Houston). Four iPSC lines were derived in our laboratory from skin biopsies of PPMS patients through the mRNA/miRNA method (Stemgent).

hPSC Culture Conditions hESC and hiPSC lines were cultured and expanded with HUESM (HUman Embryonic Stem Medium) medium and 10 ng/ml bFGF (Stemcell Technologies) onto mouse embryonic fibroblast (MEF) layer. For oligodendrocyte differentiation, cells were adapted to cultures onto MATRIGEL®-coated dishes and mTeSR1 medium (Stemcell Technologies). HUESM is composed by Knockout-DMEM, 20% Knock-out serum, glutamax 2 mM, NEAA 0.1 mM, 1× P/S and β-mercaptoethanol 0.1 mM, all purchased from Life Technologies (Grand Island, N.Y.). At all stages of differentiation cells are cultured in 5% $CO_2$ incubators.

Detailed Differentiation Protocol

PSCs were plated on MATRIGEL® (BD Biosciences; San Jose, Calif.) at a density of $10×10^3$ cells/cm$^2$ in mTeSR1 medium (Stemcell Technologies; Vancouver, BC, Canada) containing 10 μM ROCK inhibitor, Y-27632 (Stemgent; Cambridge, Mass.) for 24 hours. This density of plated hPSCs was optimized to give a confluent well by day 8 and multilayered structures at day 12 of differentiation. This set up does not require significant PSC expansion, as only one well (80% confluent) of a 6-well plate contains enough cells to differentiate and isolate at least $2×10^6$ oligodendrocytes. Cells were incubated for 1-2 days, until hPSC colonies reached a diameter of 100-250 μm.

At the day of differentiation induction (day 0), medium was switched to Neural Induction Medium, which is mTeSR Custom Medium (Stemcell Technologies) containing the small molecules SB431542 10 μM (Stemgent) and LDN193189 250 nM (Stemgent), as well as 100 nM all-trans-RA (Sigma-Aldrich; St. Louis, Mo.). mTeSR Custom Medium has the same composition as the commercially available mTeSR-1 medium but without five factors that sustain pluripotency, namely lithium chloride, GABA, pipecolic acid, bFGF, and TGFβ1 (Stemcell Technologies). Instead of mTeSR Custom Medium, we could also use DMEM/F12 with the addition of about 25 μg/ml insulin. Media changes were performed daily until day 8, with fresh RA, SB431542, and LDN193189 added to the medium every day.

By day 8 cells should be confluent and PAX6 expression should be at its peak (FIG. 7A). At day 8, the medium was switched to $N_2$ Medium containing 100 nM RA, 1 μM SAG (EMD Millipore; Billerica, Mass.) or 100 ng/ml rhSHH (R&D Systems; Minneapolis, Minn.), changed daily, with fresh RA and SAG added to the medium every day.

By day 12, overconfluent cells were piling up and 3D structures were clearly visible (FIG. 7B); this is an important checkpoint before proceeding with the differentiation. Cells expressed OLIG2 and NKX2.2 (FIG. 7C). At day 12, adherent cells were detached mechanically or enzymatically to allow for sphere formation. Sphere-formation enriched for the OLIG2$^+$ progenitors. Only the OLIG2$^+$ cells aggregated into spheres, whereas the OLIG2$^-$ cells remained as single cells. We obtained the highest number of spheres, and ultimately of O4$^+$ cells, using mechanical dispersion of the monolayer. We obtained more uniform spheres, in lower numbers, using enzymatic dispersion of the monolayer. For mechanical detachment, cells were detached using a cell lifter, breaking the monolayer of cells into small clumps so that nutrients could reach all the cells within the aggregate. Wells were inspected under the microscope to ensure that no cells were left attached. For enzymatic digestion, ACCUTASE® (1 ml/2 ml DMEM/F12 medium) was added to wells to dissociate the culture into a single-cell suspension.

Aggregates were re-plated into Ultra-low attachment plates in N$_2$B$_{27}$ Medium containing 1 µM SAG, changing it every other day. At day 20, medium was switched to PDGF Medium, and ⅔ media changes were performed every other day. During media changes, gentle pipetting was used to break apart any aggregates sticking to one another. At day 30, spheres were plated onto plates coated with poly-L-ornithine hydrobromide (50 µg/ml; Sigma-Aldrich) and Laminin (20 µg/ml; Life Technologies) at a density of 2 spheres/cm$^2$ (about 20 spheres per well in a 6-well plate). This density was optimized to allow cells to migrate out from the sphere, proliferate and spread to the entire dish by the end of the protocol without the need for passaging. We used a p200 pipette to pick aggregates that were round, golden/brown with a dark center, having a diameter between 300 and 800 µm (FIG. 7D). We avoided spheres that were completely transparent, as these do not differentiate to oligodendrocytes.

At this stage, plated spheres were cultured in a medium containing mitogens (Option A) or in a medium without any mitogens (Option B). Option A was optimized to obtain the highest yield of O4$^+$ cells, while Option B was developed to provide a shorter and less costly version of the protocol.

Option A

Spheres were plated on pO/L plates, as described above, in PDGF Medium at day 30, changing ⅔ of the PDGF Medium every other day until day 75 of differentiation. The appearance of O4$^+$ cells was assessed by live O4 staining from day 55 onwards (FIG. 6). At day 75, O4$^+$ OPCs could be isolated by FACS (FIG. 7I). Alternatively, for terminal oligodendrocyte differentiation (FIG. 7G-7H), cells were cultured in Glial Medium from day 75, changing ⅔ of the medium every 3 days for two weeks.

Option B

Figures 6A, 6B, 6C, 6D, 6E, 6F, 6G:
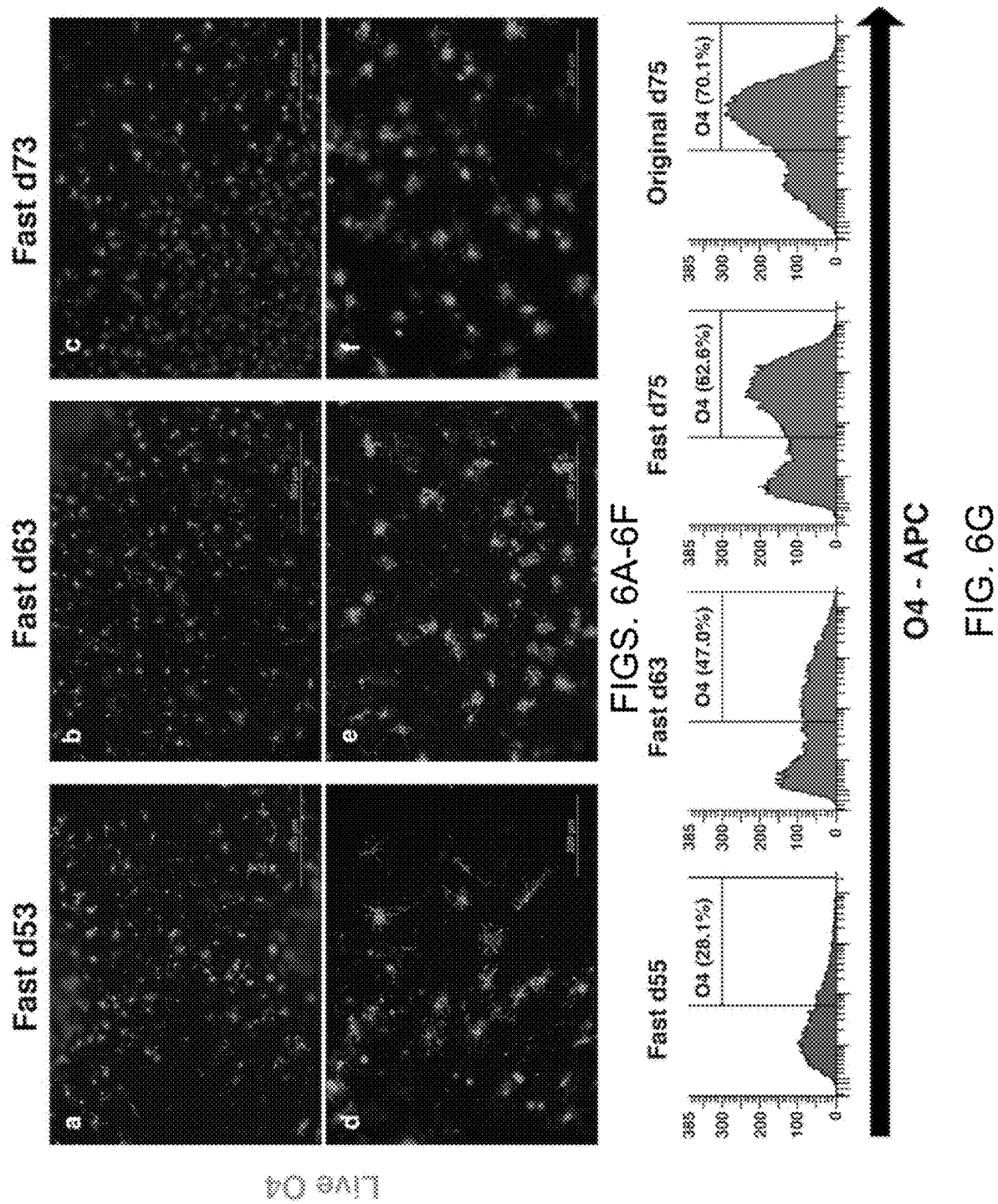
FIGS. 6A-6G shows live O4 imaging at day 53 (FIG. 6A, FIG. 6D), day 63 (FIG. 6B, FIG. 6E), and day 73 (FIG. 6C, FIG. 6F) of differentiation following the Option B protocol.

Spheres were plated on pO/L plates, as described above, in Glial Medium at day 30, changing ⅔ of the Glial Medium every other day until day 55 of differentiation. At day 55, O4$^+$ cells were visualized by live O4 staining (FIG. 6A-6F, FIG. 7F) or isolated by FACS (FIG. 6G). At day 75, O4+ OPCs could be isolated by FACS. Alternatively, cultures were kept in Glial Medium until day 75 to increase the efficiency of O4+ cells (FIG. 6). We observed MBP$^+$ cells beginning at about day 60.

For both Option A and Option B protocols, aggregates at day 30, and cells at the end of the differentiation could be cryopreserved with a viability >70%. Aggregates' viability is based on the number of thawed spheres that re-attach onto pO/L coated dishes after thawing. The sorted O4$^+$ cells could be frozen immediately after sorting. The expected post-thaw viability of the sorted O4$^+$ cells is 70-80%.

Table 2 provides a list of media compositions used in the protocol.

TABLE 2

Detailed Composition of Culture Media

| Media | Components | Provider | Final Conc. |
|---|---|---|---|
| N$_2$ Medium | DMEM/F12 | Life Technologies | |
| | Glutamax (100×) | Life Technologies | 1× |
| | Non-Essential Amino Acids (100×) | Life Technologies | 1× |
| | β-Mercapto-ethanol (1000×) | Life Technologies | 1× |
| | Penicillin-Streptomycin (100×) | Life Technologies | 1× |
| | N$_2$ Supplement (100×) | Life Technologies | 1× |
| N$_2$B$_{27}$ | N$_2$ Medium | Life Technologies | 1× |
| | B$_{27}$ Supplement (50×) | | |
| PDGF Medium | N$_2$B$_{27}$ Medium | | |
| | PDGF | R&D Systems | 10 ng/ml |
| | IGF-1 | R&D Systems | 10 ng/ml |
| | HGF | R&D Systems | 5 ng/ml |
| | NT3 | EMD Millipore | 10 ng/ml |
| | Insulin | Sigma-Aldrich | 25 µg/ml |
| | Biotin | Sigma-Aldrich | 100 ng/ml |
| | cAMP | Sigma-Aldrich | 1 µM |
| | T3 | Sigma-Aldrich | 60 ng/ml |
| Glial Medium | N$_2$B$_{27}$ Medium | Sigma-Aldrich | 20 µg/ml |
| | Ascorbic Acid | | |
| | HEPES | Sigma-Aldrich | 10 mM |
| | Insulin | Sigma-Aldrich | 25 µg/ml |
| | Biotin | Sigma-Aldrich | 100 ng/ml |
| | cAMP | Sigma-Aldrich | 1 µM |
| | T3 | Sigma-Aldrich | 60 ng/ml |

Derivation of Skin Fibroblasts from Punch Biopsies

Skin biopsies were obtained from MS patients and healthy individuals (FIG. 13). Four de-identified patients at the Tisch Multiple Sclerosis Research Center of New York were diagnosed with PPMS according to the standard diagnostic criteria. Their biopsies were obtained upon institutional review board approval (BRANY) and informed consent. All patients are Caucasian. Patients 102 and 107 are male, 56 and 61 years old respectively; patients 104 and 109 are female, 62 and 50 years old respectively.

Skin biopsies of 3 mm were collected in Biopsy Collection Medium, consisting of RPMI 1460 (Life Technologies) and 1× Antibiotic-Antimycotic (Life Technologies). Biopsies were sliced into smaller pieces (<1 mm) and plated onto a TC-treated 35 mm dish for 5 minutes to dry and finally they were incubated in Biopsy Plating Medium, composed by Knockout DMEM, 2 mM GLUTAMAX™, 0.1 mM NEAA, 0.1 mM β-Mercaptoethanol, 10% Fetal Bovine Serum (FBS), 1× Penicillin-Streptomycin (P/S; all from Life Technologies) and 1% Nucleosides (EMD Millipore), for 5 days or until the first fibroblasts grew out of the biopsy. Alternatively, biopsies were digested with 1000 U/ml Collagenase 1A (Sigma-Aldrich) for 1.5 hours at 37° C., washed, collected and plated onto 1% gelatin-coated 35 mm dish in Biopsy Plating Medium for 5 days. Fibroblasts were then expanded in Culture Medium, consisting of DMEM (Life Technologies), 2 mM GLUTAMAX™, 0.1 mM NEAA, 0.1 mM β-Mercaptoethanol, 10% FBS and 1× P/S changing medium every other day.

Reprogramming of Skin Fibroblasts

Figures 14A, 14B, 14C, 14D:
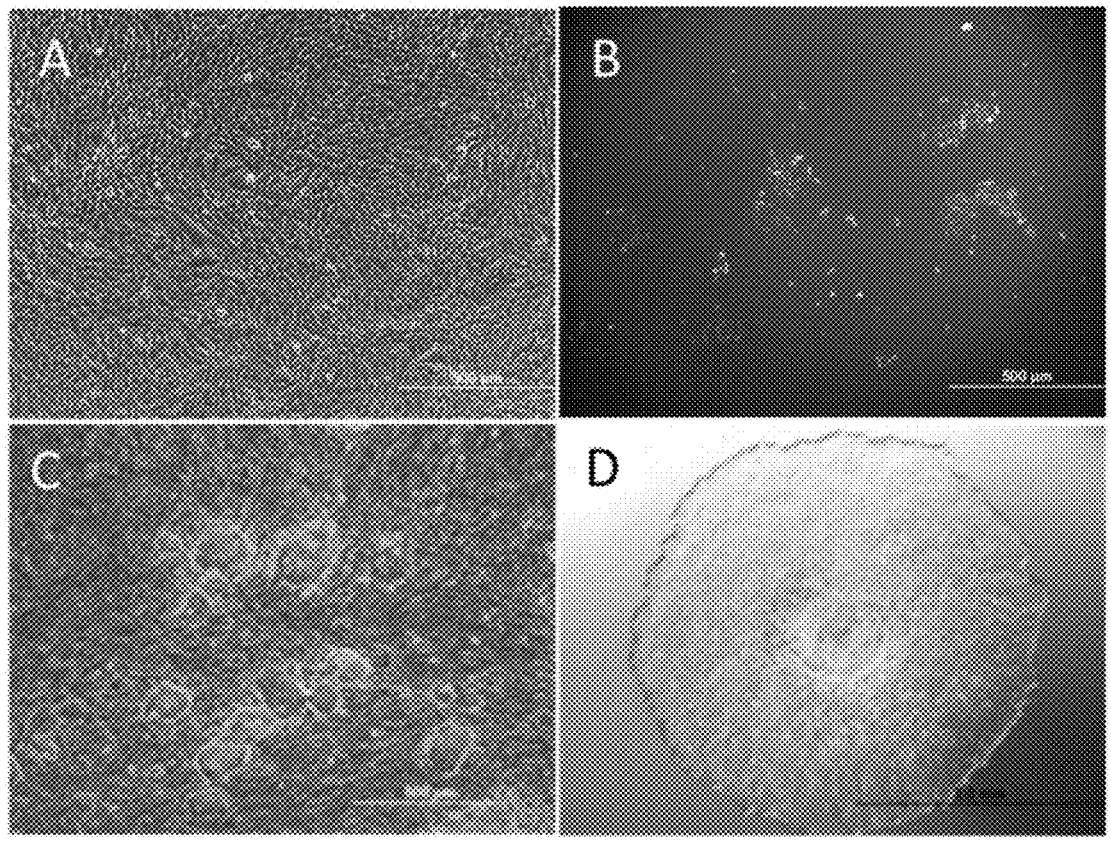
FIGS. 14A-14D show reprogramming of skin fibroblasts to iPSCs.

Skin fibroblasts at passage 3 to 5 were reprogrammed using the Stemgent mRNA/miRNA kit, which results in the generation of integration-free, virus free human iPSCs, through modified RNAs for OCT4, SOX2, KLF4, cMYC and LIN28 (FIG. 14). The addition of a specific cluster of miRNA has been found to increase the efficiency of reprogramming (Stemgent). Briefly, fibroblasts were plated onto Matrigel-coated 6-well or 12-well plates in a $5.5\times10^3$ cells/cm² density in culture medium. The following day, medium was replaced with NuFF-conditioned Pluriton reprogramming medium containing B18R. Cells were transfected for 11 consecutive days using STEMFECT™ as following: day 0 miRNA only, day 1 to day 3 mRNA cocktail only, d4 miRNA plus mRNA cocktail, day 5 to day 11 mRNA cocktail only. After day 11, visible colonies positively stained for live TRA-1-60 were picked and re-plated on MEFs with HUESM medium.

Teratoma Assay

Experiments were performed according to a protocol approved by the Columbia Institutional Animal Care and Use Committee (IACUC).

iPSC colonies were dissociated using Collagenase (Sigma-Aldrich) for 15 minutes at 37° C., washed, collected, and re-suspended in 200 µl HUESM. Cells were then mixed with 200 µl Matrigel™ (BD Biosciences) on ice, and were injected subcutaneously into immunodeficient mice (Jackson Laboratory; Bar Harbor, Me.). Teratomas were allowed to grow for 9-12 weeks, isolated by dissection, and fixed in 4% PFA overnight at 4° C. Fixed tissues were embedded in paraffin, sectioned at 10 µm thickness, and stained with hematoxylin and eosin (H&E).

Spontaneous Differentiation In Vitro iPSCs were dissociated with ACCUTASE® (Life Technologies) for 5 minutes at 37° C. and seeded into Ultra-Low attachment 6-well plates in HUESM without bFGF, changing media every other day. After 3 weeks of culture, embryoid bodies (EBs) were plated onto 1% gelatin-coated TC-treated dishes for another 2 weeks. EBs and their outgrowth were fixed in 4% PFA for 8 minutes at RT and immunostained for the appropriate markers.

RNA Isolation and qRT-PCR

RNA isolation was performed using the RNeasy Plus Mini Kit with QIAshredder (Qiagen; Hilden, Germany). Briefly, cells were pelleted, washed with PBS, and re-suspended in lysis buffer. Samples were then stored at −80° C. until processed further according to manufacturer's instructions. RNA was eluted in 30 µl RNase free ddH$_2$O and quantified with a NanoDrop 8000 spectrophotometer (Thermo Scientific; Somerset, N.J.).

For qRT-PCR, cDNA was synthesized using the GoScript™ Reverse Transcription System (Promega; Madison, Wis.) with 0.5 µg of RNA and random primers. 20 ng of cDNA were then loaded to a 96-well reaction plate together with 10 µl GoTaq® qPCR Master Mix and 1 µl of each primer (10 nM) in a 20 µl reaction and the plate was ran in Stratagene Mx300P qPCR System (Agilent Technologies; Santa Clara, Calif.). Table 3 lists primer sequences.

TABLE 3

Sequences of Primers Used for qRT-PCR

| SEQ ID. NO. | Target Gene | Forward Primer | SEQ ID. NO. | Reverse Primer |
|---|---|---|---|---|
| 1 | PAX6 | TTTGCCCGAGAAAGACTAGC | 2 | CATTTGGCCCTTCGATTAGA |
| 3 | OLIG2 | TGCGCAAGCTTTCCAAGA T | 4 | CAGCGAGTTGGT GAGCATGA |
| 5 | NKX2.2 | GACAACTGGTGGCAGATTTCGCTT | 6 | AGCCACAAAGAAAGGAGTTGGACC |
| 7 | PTCH1 | ATCTGCACCGGCCCAGCTACT | 8 | CCACCGCGAAGGCCCCAAATA |
| 9 | SHH | AAACACCGGAGCGGACAGGC | 10 | GGTCGCGGTCAGACGTGGTG |

Nanostring Analysis for Pluripotency

Figure 15A:
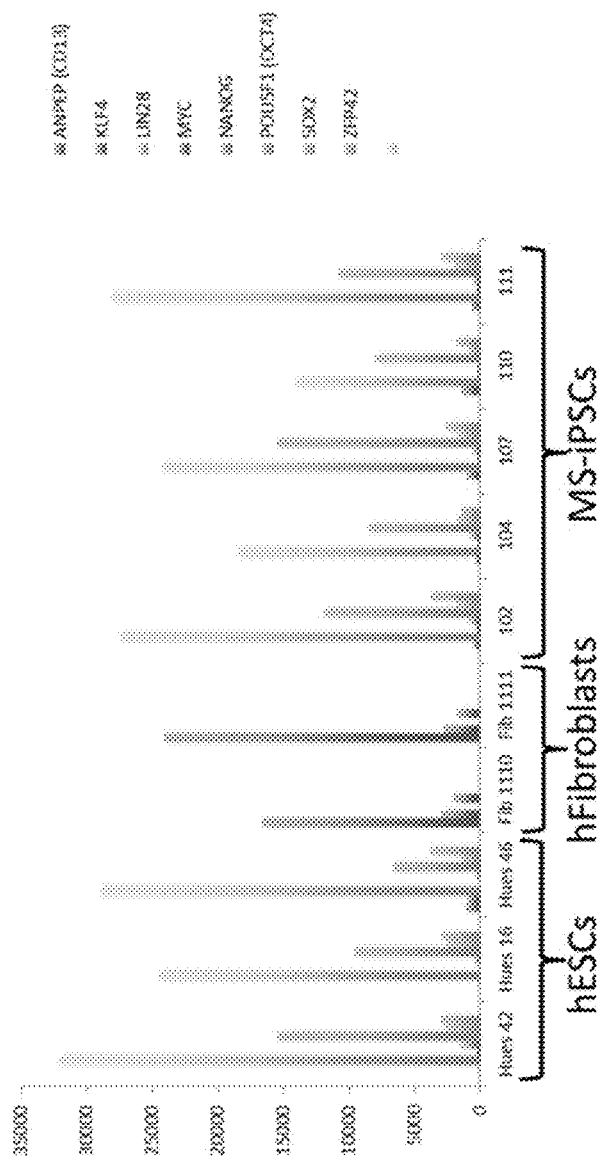
FIGS. 15A-15B show characterization of iPSC lines using nanostring analysis for pluripotency.
Figure 15B:
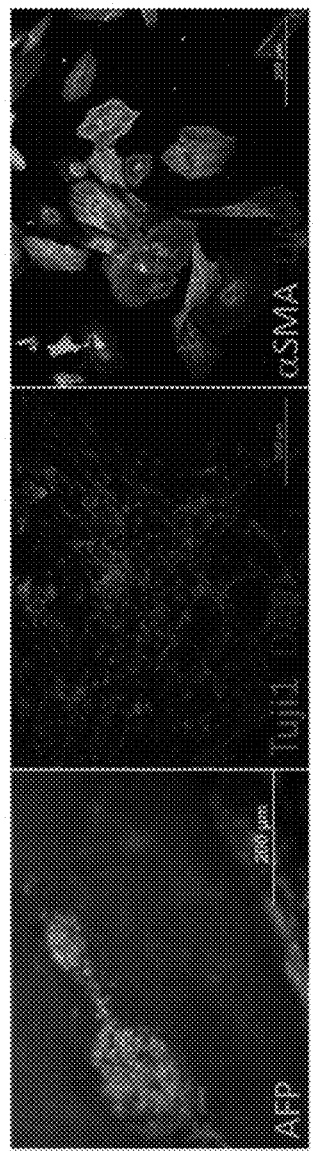

RNA was isolated from undifferentiated iPSCs and hESC HUES45 as previously described. RNA (100 ng/sample) was loaded for the hybridization with the specific Reporter Code Set and Capture Probe Set (NanoString Technologies; Seattle, Wash.) according to manufacturer's instructions. Data were normalized to the following housekeeping genes: ACTB, POLR2A, ALAS1. Data were expressed as fold changes to the expression of the hESC line (HUES45=1). See FIG. 15.

Karyotyping

All iPSC-lines were subjected to cytogenetic analysis by Cell Line Genetics to confirm a normal karyotype.

Immunostaining and Imaging

Cells were washed 3× in PBS-T (PBS containing 0.1% Triton-X100) for 10 minutes, incubated for 2 hours in blocking serum (PBS-T with 5% goat or donkey serum) and primary antibodies were applied overnight at 4° C. (Table 4). The next day, cells were washed 3× in PBS-T for 15 minutes, incubated with secondary antibodies for 2 hours at room-temperature (RT), washed 3× for 10 minutes in PBS-T, counterstained with DAPI for 15 minutes at RT and washed 2× in PBS. Invitrogen™ Alexa Fluor secondary antibodies, goat or donkey anti-mouse, rat, rabbit, goat and chicken 488, 555, 568, and 647 were used at 1:500 dilution (Life Technologies).

Images were acquired using an Olympus IX71 inverted microscope, equipped with Olympus DP30BW black and white digital camera for fluorescence and DP72 digital color camera for H&E staining. Fluorescent colors were digitally applied using the Olympus software DP Manager or with ImageJ. For counting, at least three non-overlapping fields were imported to ImageJ, thresholded and scored manually.

Flow Cytometry

Cells were enzymatically harvested by ACCUTASE® treatment for 25 min at 37° C. to obtain a single cell suspension. Cells were then re-suspended in 100 µl of their respective medium containing the appropriate amount of either primary antibody or fluorescence-conjugated antibodies and were incubated on ice for 30 minutes shielded from light. When secondary antibodies were used, primary antibodies were washed with PBS and secondary antibodies were applied for 30 minutes on ice. Stained or GFP expressing cells were washed with PBS and sorted immediately on a 5 laser BD Biosciences ARIA-IIu™ Cell Sorter using the 100 μm ceramic nozzle, and 20 psi. DAPI was used for dead cell exclusion. Flow cytometry data were analyzed using BD FACSDiva™ software.

Transplantation into Shiverer (shi/shi)×Rag2$^{-/-}$ Mice

All experiments using shiverer/rag2 mice (University of Rochester; Windrem, M. S. et al., *Cell Stem Cell*. 2:553-565 (2008)) were performed according to protocols approved by the University at Buffalo Institutional Animal Care and Use Committee (IACUC). FACS-sorted O4$^+$ OPCs that had been previously cryopreserved were thawed and allowed to recover for 1-2 days prior to surgery by plating on pO/L dishes in PDGF Medium. Cells were prepared for injection by re-suspending cells at $1\times10^5$ cells per μl.

Injections were performed as previously described. Sim, F. J. et al. (2011). Pups were anesthetized using hypothermia and $5\times10^4$ cells were injected in each site, bilaterally at a depth of 1.1 mm into the corpus callosum of postnatal day 2-3 pups. Cells were injected through pulled glass pipettes, inserted directly through the skull into the presumptive target sites. Animals were sacrificed and perfused with saline followed by 4% paraformaldehyde at 12-16 weeks. Cryopreserved coronal sections of mouse forebrain (16 μm) were cut and sampled every 160 μm. Sim, F. J. et al. (2011). Human cells were identified with mouse antihuman nuclei (hNA) and myelin basic protein-expressing oligodendrocytes were labeled with MBP. Human astrocytes and OPCs were stained with human-specific antibodies against hGFAP and hNG2 respectively. Mouse neurofilament (NF) was stained by 1:1 mixture of SMI311 and SMI312. Invitrogen™ Alexa Fluor secondary antibodies, goat anti-mouse 488, 594, and 647 were used at 1:500 dilution (Life Technologies). For transmission electron microscopy, tissue was processed as described previously. Sim, F. J. et al., *Molec. Cell. Neurosci.* 20:669-682 (2002). Table 4 provides a list of primary antibodies used.

TABLE 4

| Primary Antibodies | | | |
| --- | --- | --- | --- |
| Antigen | Dil. | Host | Provider |
| OCT4 | 1:250 | Rabbit | Stemgent |
| TRA-1-60 | 1:250 | Mouse | Millipore |
| SOX2 | 1:250 | Rabbit | Stemgent |
| TRA-1-81 | 1:250 | Mouse | Millipore |
| NANOG | 1:100 | Rabbit | Cell Signal. |
| SSEA4 | 1:250 | Mouse | Abcam |
| AFP | 1:300 | Rabbit | Dako |
| αSMA | 1:300 | Mouse | Sigma |
| βIII-Tubulin | 1:500 | Chicken | Neuromics |
| PAX6 | 1:250 | Rabbit | Covance |

TABLE 4-continued

| Primary Antibodies | | | |
| --- | --- | --- | --- |
| Antigen | Dil. | Host | Provider |
| OLIG2 | 1:500 | Rabbit | Millipore |
| NKX2.2 | 1:75 | Mouse | DSHB |
| SOX10 | 1:100 | Goat | R&D Sys. |
| NG2 | 1:200 | Mouse | BD Biosci. |
| PDGFRα-PE | 1:5 | Mouse | BD Biosci. |
| O4 | 1:30 | Mouse | Goldman lab |
| MBP | 1:200 | Rat | Millipore |
| MAP2 | 1:5000 | Chicken | Abcam |
| GFAP | 1:750 | Rabbit | Dako |
| hNA clone 235-1 | 1:100 | Mouse | Millipore |
| GFAP (in vivo) | 1:800 | Mouse | Covance |
| NG2 (in vivo) | 1:800 | Mouse | Millipore |
| SMBI311, SMBI312 (mNeurofilament) | 1:800 | Mouse | Covance |

REFERENCES

In addition to the documents cited in other sections of this disclosure, the following references may provide additional context. All of the references cited in this disclosure are hereby incorporated by reference in their entireties. In addition, any manufacturer's instructions or catalogues for any products cited or mentioned herein are incorporated by reference. Documents incorporated by reference into this text, or any teachings therein, can be used in the practice of the present invention. Documents incorporated by reference into this text are not admitted to be prior art.

Antel, J. et al., *Acta Neuropathol.* 123:627-638 (2012).
Boulting, G. L. et al., *Nat. Biotechnol.* 29:279-286 (2011).
Hauser, S. L. et al., *Ann Neurol.* 74:317-327 (2013).
Hu, Z. et al., *Differentiation* 78:177-184 (2009).
Miller, R. H. et al., *J. Neurosci. Res.* 76:9-19 (2004).
Patani, R. et al., Nature Communications 2:214 (2011).
Rice, C. M. et al., *J. Neurol. Neurosurg. Ps.* 84:1100-1106 (2013).
Tomassy, G. S. et al., Frontiers Cell. Neurosci. 8:201 (2014).
Yamada M. et al., *Nature* 510:533-536 (2014).

The foregoing description of the specific embodiments will fully reveal the general nature of the invention such that others can, without undue experimentation, apply knowledge that is within the ordinary skill of those in the art to readily modify and/or adapt such specific embodiments for various applications without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The present invention is further described by the following claims.

What is claimed is:

1. A method of generating oligodendrocytes, the method comprising:
   a) culturing PSCs in an adherent culture as a monolayer in a medium comprising a low concentration of RA, (i) with dual SMAD inhibition comprising inhibition of both activin/nodal/TGFβ signaling and BMP signaling from day 0 to day 8, and (ii) with SHH or an agonist of Smoothened from day 8 to day 12, to produce OLIG2+ cells;
   b) enriching for OLIG2+ cells by culturing the cells of step (a) in suspension (i) from day 12 to day 20 in a medium comprising SHH or an agonist of Smoothened and a low concentration of RA, and (ii) from day 20 to day 30 in a medium comprising PDGF, HGF, IGF-1, and NT3; and
   c) culturing the cells of step (b) in an adherent culture in a medium comprising AA and lacking PDGF, HGF, IGF-1, and NT3 from day 30 to day 60;
   thereby generating oligodendrocytes.

2. The method of claim 1, wherein the PSCs are embryonic stem cells.

3. The method of claim 1, wherein the PSCs are induced pluripotent stem cells (iPSCs).

4. The method of claim 3, wherein the iPSCs are derived from a patient with multiple sclerosis.

5. The method of claim 1, wherein the PSCs are mammalian cells.

6. The method of claim 1, wherein the PSCs are cultured in a medium comprising an inhibitor of rho-associated protein kinase (ROCK).

7. The method of claim 1, wherein dual SMAD inhibition is by SB431542 and LDN193189.

8. The method of claim 1, wherein the cells are PAX6+ by day 8.

9. The method of claim 1, wherein the agonist of Smoothened is SAG.

10. The method of claim 1, wherein the concentration of RA is about 100 nM.

11. The method of claim 1, wherein the cells of (c) are cultured on a surface comprising an extracellular matrix protein and a positively charged poly-amino acid.

12. The method of claim 11, wherein the extracellular matrix protein is laminin.

13. The method of claim 11, wherein the poly-amino acid is poly-ornithine.

14. The method of claim 1, wherein at least 50% of the cells are OLIG2+ by day 12.

15. The method of claim 1, wherein at least 60% of the cells are OLIG2+ by day 12.

16. The method of claim 1, wherein at least 70% of the cells are OLIG2+ by day 12.

17. The method of claim 1, wherein at least 20% of the cells are MBP+ at day 60.

18. The method of claim 1, wherein at least 25% of the cells are MBP+ at day 60.

19. The method of claim 1, wherein at least 30% of the cells are MBP+ at day 60.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Primer

```
<400> SEQUENCE: 1
tttgcccgag aaagactagc                                              20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
catttggccc ttcgattaga                                              20

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
tgcgcaagct ttccaagat                                               19

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
cagcgagttg gtgagcatga                                              20

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
gacaactggt ggcagatttc gctt                                         24

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
agccacaaag aaaggagttg gacc                                         24

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
atctgcaccg gcccagctac t                                            21

<210> SEQ ID NO 8
<211> LENGTH: 21
```

```
<212> TYPE: DNA
<213> ORGANISM: Artificial Sequence
<220> FEATURE:
<223> OTHER INFORMATION: Primer

<400> SEQUENCE: 8
ccaccgcgaa ggccccaaat a                                           21

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
aaacaccgga gcggacaggc                                             20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ggtcgcggtc agacgtggtg                                             20
```